(12) United States Patent
Collu et al.

(10) Patent No.: US 12,384,990 B2
(45) Date of Patent: Aug. 12, 2025

(54) TREATMENT COMPOSITIONS COMPRISING PLANT ROSIN MATERIAL AND CERTAIN PERFUME RAW MATERIALS

(71) Applicant: The Procter & Gamble Company, Cincinnati, OH (US)

(72) Inventors: Mattia Collu, Saint-Gilles (BE); Cédric Marc Tahon, Oost-Vlaanderen (BE); Johan Smets, Lubbeek (BE); Nans Elian Ravidat, Brussels (BE); Prakash J. Madhav, Maineville, OH (US); Hugo Robert Germain Denutte, Hofstade (BE)

(73) Assignee: The Procter & Gamble Company, Cincinnati, OH (US)

( * ) Notice: Subject to any disclaimer, the term of this patent is extended or adjusted under 35 U.S.C. 154(b) by 741 days.

(21) Appl. No.: 17/549,923

(22) Filed: Dec. 14, 2021

(65) Prior Publication Data
US 2022/0195348 A1    Jun. 23, 2022

Related U.S. Application Data

(60) Provisional application No. 63/125,988, filed on Dec. 16, 2020.

(51) Int. Cl.
| | | |
|---|---|---|
| C11D 1/00 | (2006.01) |
| B08B 3/04 | (2006.01) |
| C11D 3/00 | (2006.01) |
| C11D 3/38 | (2006.01) |
| C11D 3/382 | (2006.01) |
| C11D 3/50 | (2006.01) |

(52) U.S. Cl.
CPC ............ C11D 3/382 (2013.01); C11D 3/0015 (2013.01); C11D 3/50 (2013.01)

(58) Field of Classification Search
CPC ....... C11D 1/00; C11D 3/0015; C11D 3/2065; C11D 3/2093; C11D 3/38; C11D 3/382; C11D 3/50; C11D 3/505; B08B 3/04
See application file for complete search history.

(56) References Cited

U.S. PATENT DOCUMENTS

| | | |
|---|---|---|
| 2,571,689 A | 10/1951 | Maria et al. |
| 2,776,276 A | 1/1957 | Glasebrook et al. |
| 3,950,510 A | 4/1976 | Adams |
| 5,362,715 A | 11/1994 | Cohen |
| 5,478,567 A | 12/1995 | Nakagawa et al. |
| 6,869,923 B1 | 3/2005 | Cunningham |
| 7,438,897 B2 | 10/2008 | Gupta |
| 7,795,476 B2 | 9/2010 | Corzani |
| 8,802,729 B2 | 8/2014 | Fenyvesi et al. |
| 9,186,642 B2 | 11/2015 | Dihora |
| 10,582,705 B2 | 3/2020 | Conover |
| 2002/0018760 A1 | 2/2002 | Vatter et al. |
| 2004/0121926 A1 | 6/2004 | Waits et al. |
| 2006/0020057 A1 | 1/2006 | Maas et al. |
| 2006/0154850 A1* | 7/2006 | Quellet .................. C11D 3/502 512/2 |
| 2007/0129476 A1 | 6/2007 | Macbeath et al. |
| 2010/0089420 A1 | 4/2010 | Greenberg |
| 2013/0125297 A1 | 5/2013 | Pagani |
| 2019/0153354 A1 | 5/2019 | Lankin et al. |
| 2019/0373883 A1 | 12/2019 | Conover |

FOREIGN PATENT DOCUMENTS

| | | | |
|---|---|---|---|
| EP | 138597 | * 4/1985 | ............. C11D 17/00 |
| EP | 0138597 A2 | 4/1985 | |
| EP | 1038910 A1 | 9/2000 | |
| GB | 1340043 A | 12/1973 | |
| GB | 1349741 A | 4/1974 | |
| GB | 1419116 A | 12/1975 | |
| GB | 1515299 A | 6/1978 | |
| IT | 202000004684 A1 | 9/2021 | |
| JP | 2001262199 A | 9/2001 | |
| WO | 2011030158 A2 | 3/2011 | |
| WO | 2019051165 A1 | 3/2019 | |
| WO | 2020058373 A1 | 3/2020 | |
| WO | 2020234263 A1 | 11/2020 | |

OTHER PUBLICATIONS

All Office Actions; U.S. Appl. No. 17/549,922, filed Dec. 14, 2021.
All Office Actions; U.S. Appl. No. 17/549,916, filed Dec. 14, 2021.
All Office Actions; U.S. Appl. No. 17/549,919, filed Dec. 14, 2021.
Glycerol ester of wood rosin INV, XP55811290 Retrieved from the Internet URL:https://en.wikipedia.org/wiki/Glycerolester of wood rosin, dated Mar. 4, 2021, p. 2.
Database GNPD Mintel, "Moist Diane Extra Moist & Shine Hair Mask has been relaunched", http:llwww.gnpd.com T, dated Jan. 29, 2020 pp. 3.
Eastman rosin products, "Natural resins for adhesion, wetting, viscocity control", pp. 8.
Mahmoud Abdul-Raheim,"BAOJ Chemistry Rosin Chemistry, Derivatives, and Applications a review", vol. 4, dated 2018, p. 2 of 16.
Polymer Properties Database, "Rosin Esters and Polymers", https://polymerdatabase.com/polymer classes/Rosin.html, dated 2015, pp. 03.
Satish Kumar Gupta,"Rosin: A naturally derived excipient in drug delivery systems, Department of Pharmaceutical Technology", dated 2013, pp. 05.
Unpublished U.S. Appl. No. 17/549,916, filed Dec. 14, 2021, to first inventor Mattia Collu et al.
Unpublished U.S. Appl. No. 17/549,919, filed Dec. 14, 2021, to first inventor Mattia Collu et al.
Unpublished U.S. Appl. No. 17/549,922, filed Dec. 14, 2021, to first inventor Mattia Collu et al.
15940 PCT Search Report and Written Opinion for PCT/US2021/072891 dated Apr. 19, 2022, 17 pages.
Bambang Wiyono et al. "Chemical Compositions of Pine Resin, Rosin and Turpentine Oil from West Java", Journal of Forestry Research, vol. 3, No. 1, dated Mar. 1, 2016; pp. 7-17.

(Continued)

*Primary Examiner* — Brian P Mruk
(74) *Attorney, Agent, or Firm* — Carolyn S. Powell; George H. Leal

(57) ABSTRACT

Treatment compositions that include plant rosin materials and certain perfume raw materials, which may be characterized by certain structural moieties and/or molecular descriptors. Related methods of making and using such compositions.

13 Claims, No Drawings

(56) References Cited

OTHER PUBLICATIONS

Database GNPD Mintel; "Foundation EX SPF 50+ PA++++", http://www.gnpd.com, dated May 2020; 5 Pages.
Database GNPD Mintel; "Hair Color Treatment", http://www.gnpd.com; dated Nov. 17, 2016; 4 Pages.
Database GNPD Mintel; "Light Luminous Hydrating Lipstik" http://www.gnpd.com; dated Jul. 1, 2020; 4 Pages.
Database GNPD Mintel; "Moisturizing Lip Balm", http;//www.gnpd.com, dated Nov. 10, 2020 , 3 Pages.
Database GNPD Mintel; "Shaving Oil", http://www.gnpd.com, dated May 2, 2018 , 5 Pages.

* cited by examiner

TREATMENT COMPOSITIONS COMPRISING PLANT ROSIN MATERIAL AND CERTAIN PERFUME RAW MATERIALS

CROSS REFERENCE TO RELATED APPLICATION

This application claims benefit of Provisional Application Ser. No. 63/125,988, filed on Dec. 16, 2020.

FIELD OF THE INVENTION

The present disclosure relates to treatment compositions that include plant rosin materials and certain perfume raw materials, which may be characterized by certain structural moieties and/or molecular descriptors. The present disclosure also relates to related methods of making and using such compositions.

BACKGROUND OF THE INVENTION

Manufacturers of treatment compositions, such as consumer products like fabric enhancers and laundry detergents, are continually seeking ways to improve perfume delivery. Core-shell capsules have been employed in the past, but such delivery particles typically require substantial investment on the process side and may be provided as slurries that bring undesired water levels to certain products. Thus, there is a desire for alternatives to core-shell capsules.

Perfume delivery particles that use certain amphiphilic graft co-polymers are discussed in the art, but these polymers are synthetic, which may not be preferred. Instead, manufacturers may seek perfume delivery systems that are derived from natural/sustainable sources or feedstock materials.

Additionally, while much attention is often paid to the perfume delivery mechanism, for example the capsule or the polymer, less attention has been given to the perfumes being delivered. In order to maximize the efficiency of the perfume delivery, it would be desirable to formulate a fragrance with perfume materials that are most likely to interact with the delivery system in an efficacious way. However, depending on the system, there may be little direction offered to the formulator.

In view of the foregoing, there is a need for treatment compositions that include improved perfume delivery systems, particularly those derived from natural materials and that use preferred perfume raw materials for effective delivery and performance.

SUMMARY OF THE INVENTION

The present disclosure relates to treatment compositions that include a plant rosin material and certain perfume raw materials.

For example, the present disclosure relates to a treatment composition that includes a plant rosin material and a fragrance material, where the fragrance material includes one or more perfume raw materials, where the one or more perfume raw materials includes a moiety selected from the group consisting of a cycloalkane moiety, a cycloalkene moiety, a branched alkane moiety, and combinations thereof.

The present disclosure also relates to a treatment composition that includes a plant rosin material and a fragrance material, where the fragrance material includes one or more perfume raw materials characterized by one of the molecular descriptors/parameters, determined according to the test methods described herein; for example, (a) a SsssCH value of ≥0.681852, preferably additionally characterized by a Gmin <−0.10643; or (b) a SsssCH value of <0.682 and a dxp10 value of <−0.00709584.

The present disclosure also relates to methods of treating a surface, preferably a fabric, where the method includes the step of contacting the surface with the treatment composition according to the present disclosure, optionally in the presence of water.

DETAILED DESCRIPTION OF THE INVENTION

The present disclosure relates to treatment compositions that include a plant rosin material and a fragrance material. The fragrance material comprises certain perfume raw materials that are carefully selected for their ability to interact with the plant rosin material effectively and provide good performance in terms of stability, deposition, and/or release.

Without wishing to be bound by theory, it is believed that perfume raw materials ("PRMs") that are characterized by certain structures or other characteristics are more likely to associate with the plant rosin material compared to other PRMs, which is further believed to lead to improved deposition on a target surface, such as a fabric. When co-formulated into a base composition, or even added concurrently as a premix, the resulting treatment composition can provide improved freshness performance.

The compositions, components, and processes of the present disclosure are discussed in more detail below.

As used herein, the articles "a" and "an" when used in a claim, are understood to mean one or more of what is claimed or described. As used herein, the terms "include," "includes," and "including" are meant to be non-limiting. The compositions of the present disclosure can comprise, consist essentially of, or consist of, the components of the present disclosure.

The terms "substantially free of" or "substantially free from" may be used herein. This means that the indicated material is at the very minimum not deliberately added to the composition to form part of it, or, preferably, is not present at analytically detectable levels. It is meant to include compositions whereby the indicated material is present only as an impurity in one of the other materials deliberately included. The indicated material may be present, if at all, at a level of less than 1%, or less than 0.1%, or less than 0.01%, or even 0%, by weight of the composition.

As used herein "consumer product," means baby care, beauty care, fabric & home care, family care, feminine care, and/or health care products or devices intended to be used or consumed in the form in which it is sold, and not intended for subsequent commercial manufacture or modification. Such products include but are not limited to diapers, bibs, wipes; products for and/or methods relating to treating human hair, including bleaching, coloring, dyeing, conditioning, shampooing, styling; deodorants and antiperspirants; personal cleansing; skin care including application of creams, lotions, and other topically applied products for consumer use; and shaving products, products for and/or methods relating to treating fabrics, hard surfaces and any other surfaces in the area of fabric and home care, including: air care, car care, dishwashing, fabric conditioning (including softening), laundry detergency, laundry and rinse additive and/or care, hard surface cleaning and/or treatment, and other cleaning for consumer or institutional use; products and/or methods relating to bath tissue, facial tissue, paper handkerchiefs, and/or paper towels; tampons, feminine napkins; adult incontinence products; products and/or methods relating to oral care including toothpastes, tooth gels, tooth rinses, denture adhesives, tooth whitening; over-the-counter health care including cough and cold remedies; pest control products; and water purification.

As used herein the phrase "fabric care composition" includes compositions and formulations designed for treating fabric. Such compositions include but are not limited to, laundry cleaning compositions and detergents, fabric softening compositions, fabric enhancing compositions, fabric freshening compositions, laundry prewash, laundry pretreat, laundry additives, spray products, dry cleaning agent or composition, laundry rinse additive, wash additive, post-rinse fabric treatment, ironing aid, unit dose formulation, delayed delivery formulation, detergent contained on or in a porous substrate or nonwoven sheet, and other suitable forms that may be apparent to one skilled in the art in view of the teachings herein. Such compositions may be used as a pre-laundering treatment, a post-laundering treatment, or may be added during the rinse or wash cycle of the laundering operation.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C. and under the atmospheric pressure.

In all embodiments of the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Treatment Composition

The present disclosure relates to treatment compositions that comprise plant rosin materials and fragrance materials, where the fragrance material comprises certain perfume raw materials.

The treatment composition may be a consumer product composition. The consumer product composition may be a fabric care composition, a hard surface cleaner composition, a dish care composition, a hair care composition, a body cleansing composition, or a mixture thereof The consumer product composition may be a conditioning composition, such as a liquid fabric enhancer composition or a hair conditioner composition.

The treatment compositions of the present disclosure may be fabric care compositions. Such compositions may be used as a pre-laundering treatment, a post-laundering treatment, or may be added during the rinse or wash cycle of the laundering operation. The fabric care composition may be a fabric detergent composition, a fabric conditioning composition, or a mixture thereof, preferably a fabric conditioning composition. Fabric conditioning compositions may include liquid fabric softeners and liquid fabric enhancing compositions.

The treatment composition may be in any suitable form, for example in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof, preferably a liquid.

The treatment composition may be in the form of a liquid. The liquid composition may include from about 30%, or from about 40%, or from about 50%, to about 99%, or to about 95%, or to about 90%, or to about 75%, or to about 70%, or to about 60%, by weight of the composition, of water. The liquid composition may be a liquid laundry detergent, a liquid fabric conditioner, a liquid dish detergent, a hair shampoo, a hair conditioner, or a mixture thereof.

The treatment composition may be in the form of a solid. The solid composition may be a powdered or granular composition. Such compositions may be agglomerated or spray-dried. Such composition may include a plurality of granules or particles, at least some of which include comprise different compositions. The composition may be a powdered or granular cleaning composition, which may include a bleaching agent. The composition may be in the form of a bead or pastille, which may be pastilled from a liquid melt. The composition may be an extruded product.

The treatment composition may be in the form of a unitized dose article, such as a tablet, a pouch, a sheet, or a fibrous article. Unitized dose articles in the form of pouches typically include a water-soluble film, such as a polyvinyl alcohol water-soluble film, that at least partially encapsulates a composition. Suitable films are available from Mono-Sol, LLC (Indiana, USA). The composition can be encapsulated in a single or multi-compartment pouch. A multi-compartment pouch may have at least two, at least three, or at least four compartments. A multi-compartmented pouch may include compartments that are side-by-side and/or superposed. The composition contained in the pouch or compartments thereof may be liquid, solid (such as powders), or combinations thereof. Pouched compositions may have relatively low amounts of water, for example less than about 20%, or less than about 15%, or less than about 12%, or less than about 10%, or less than about 8%, by weight of the detergent composition, of water.

The treatment composition may be in the form of a spray and may be dispensed from a bottle, for example, via a trigger sprayer and/or an aerosol container with a valve.

When the treatment composition is a liquid, the composition may be characterized by a viscosity. The composition may have a viscosity of from about 1 to about 1500 centipoises (about 1-1500 mPa*s), from about 50 to about 1000 centipoises (about 50-1000 mPa*s), or from about 100 to 500 centipoises (about 100-500 mPa*s), or from about 100 to about 200 centipoises (about 100-200 mPa*s), at 20 $s^{-1}$ and 21° C., is disclosed. Relatively lower viscosities allow for improved dosing and/or less residue in a dispenser drawer. Viscosity is determined according to the method provided in the Test Methods section below.

The treatment compositions of the present disclosure may be characterized by a pH of from about 2 to about 12, or from about 2 to about 8.5, or from about 2 to about 7, or from about 2 to about 5. The treatment compositions of the present disclosure may have a pH of from about 2 to about 4, preferably a pH of from about 2 to about 3.7, more preferably a pH from about 2 to about 3.5, preferably in the form of an aqueous liquid. It is believed that such pH levels facilitate stability of certain adjuncts, such as conditioning actives (e.g., esterquats). The pH of a composition is determined by dissolving/dispersing the composition in deionized water to form a solution at 10% concentration, at about 20° C.

The treatment compositions, preferably liquid treatment compositions, of the present disclosure may comprise particles. The particles may comprise the plant resin material and the one or more benefit agents, such as perfume raw materials. When the treatment composition is in the form of a liquid, the treatment composition may further comprise a structurant. The process may comprise adding a structurant to the base composition, preferably after the one or more benefit agents and the plant rosin material have been added. The structurant may be present in an effective amount that is capable of suspending the particles in the treatment composition.

The treatment composition may comprise adjunct ingredients, many of which are described above. The adjuncts may added to the base composition before, during, or after the plant rosin material and/or the one or more benefit agents are added to the base composition. For example, neat perfume oil may be added to the base composition prior to a premix composition, where the premix composition comprises the plant rosin material and the one or more benefit agents (e.g., fragrance material). For example, perfume encapsulates may be added after such a premix is added to the base composition. A structurant may be added after the premix composition, and even after perfume encapsulates, if present.

Plant rosin materials, fragrance materials, and premixes thereof are discussed in more detail below.

Plant Rosin Material

The compositions of the present disclosure relate to plant rosin materials. It is believed that the plant rosin material will interact with the fragrance materials, as disclosed herein, to form an effective perfume delivery system.

As used herein, "plant rosin material" may include plant rosins (including resin acids), plant rosin derivatives, or mixtures thereof. Plant rosin material in the present compositions, particles, and processes can provide performance benefits, for example by facilitating improved deposition and/or stability of benefit agents. Such materials may further be preferred to known alternatives in the presently disclosed compositions and processes because they are derived from natural and/or sustainable resources.

As discussed in more detail below, plant rosin is typically derived from conifer plants (class: Pinopsida), usually from pine trees (genus: *Pinus*). Also called "colophony," plant rosin is a solid material produced by heating liquid resins to vaporize the volatile liquid terpene components. Plant rosins are typically composed of resin acids such as abietic acid and related compounds. Plant rosins may be further derivatized, for example through esterification and/or hydrogenation.

The plant rosin materials may be added at any suitable level so as to provide a benefit in the final treatment composition. For example, the plant rosin material may be added in an amount so that it is present at a level of from about from about 0.01% to about 10%, or from about 0.01% to about 5%, or from about 0.05% to about 3%, or from about 0.1% to about 1%, by weight of the final treatment composition. Adding to little may result in little to no added benefit, while adding too much may result in processing challenges.

Plant rosin materials may be characterized by a softening point. Plant rosin materials are typically solid at room temperature, but the softening point is a measure of the glass transition temperature associated with these materials. The softening point of a plant rosin material is determined according to method provided in the Test Method section below.

The plant rosin material may be characterized by a softening point of from about 50° C. to about 175° C., or from about 60° C. to about 150° C., or from about 75° C. to about 125° C. Rosins may need to be softened by heating in order to be incorporated into consumer products. Thus, for ease of processing and/or energy savings, plant rosin materials having relatively lower softening points (e.g., less than 125° C.) may be preferred for the compositions and processes of the present disclosure. Lower softening points may also have an effect on improving the deposition aid performance of the plant rosin material.

Plant rosin materials may be characterized by an acid number (sometimes called "acid value"). The acid number of a plant rosin material relates to the total free acid content of these products. The acid number of a plant rosin material is determined according to method provided in the Test Method section below.

Plant rosin materials may be characterized by an acid number less than about 175, e.g., from about 0 to about 175. For the particles, compositions, and processes of the present disclosure, it may be preferred to use plant rosin material having a relatively low acid number, such as less than about 125, preferably less than about 100, more preferably less than about 75, even more preferably less than about 50, more preferably less than about 25, so as to have minimal effect on the final pH of the treatment composition. Without being bound by theory, it is believed that plant rosin materials having a relatively low acid number may also be more easily dispersible in the base and/or treatment compositions of the present disclosure.

The color of the plant rosin material may be graded based on the Gardner Color standard number, ranging 1 to 18. So as to have minimal effect on the final color of the treatment composition, preferred plant rosin materials of the present disclosure may have a color grade of from about 1 to about 10, preferably from about 1 to about 8. The color grade of a plant rosin material is determined according to method provided in the Test Method section below.

Plant rosin materials may have an odor. Naturally derived resins have an abundance of terpenic compounds. For the compositions and processes of the present disclosure, it may be preferred to select compound with a relatively low amount of terpenic structures and/or odor, so that the naturally derived resin will not interfere with the overall character perception. On the other hand, if there is a desire for a pine-tree-like fragrance character, then the presence of terpenic structures may be preferred.

For example, gum rosins may be preferred over tall oil rosins, as tall oil rosins may include sulfur contaminants that affect the odor. On the other hand, it may be desirable for the plant rosin materials to have a detectable odor, as the "piney" scent associated with rosin material may be useful or desirable in a particular product composition.

Plant rosin materials are typically relatively insoluble in water. For example, plant resin materials according to the present disclosure may be characterized by a solubility of less than 1 g/L, or less than 100 g/L, or less than 1 g/L, or less than 0.1 g/L, or less than about 0.01 g/L, in deionized water at 22° C. Without wishing to be bound by theory, it is believed that the relatively insoluble nature of the plant rosin materials of the present disclosure contribute to the deposition efficiency and performance of the associated benefit agent.

Plant rosin materials may be characterized by a density. Typically, the plant rosin materials are characterized by a density of at greater than 1.0 kg/dm³, preferably at least 1.1 kg/dm³, at 25° C.

Plant rosin materials are typically flammable. For the particles, compositions, and processes of the present disclosure, it may be preferred to use plant rosin materials that have a relatively high flash point, e.g., higher than 190° C., to facilitate easier and safer processing. The flash point of a plant rosin material is determined according to method provided in the Test Method section below.

The processes and compositions of the present disclosure may comprise plant rosin material, where the plant rosin material may comprise a material selected from the group consisting of gum rosin, wood rosin, tall oil rosin, derivatives thereof, and mixtures thereof preferably gum rosin, derivatives thereof, and mixtures thereof; more preferably a gum rosin ester. The plant rosin material may be a plant rosin ester, preferably an ester formed from an alcohol having two or more carbon atoms, more preferably where the alcohol is glycerol, pentaerythritol, or a mixture thereof. The plant rosin material may be at least partially hydrogenated, preferably fully hydrogenated. The plant rosin material may comprise at least 50%, more preferably at least 60%, more preferably at least 70%, more preferably at least 80%, more preferably at least 85%, by weight of the plant rosin material, of an abietic-type acid, a derivative of an abietic-type acid, or a mixture thereof.

Plant rosins and plant rosin derivatives, as well as premixes comprising such substances, are discussed in more detail below.

A. Plant Rosins

The plant rosin material of the present disclosure may comprise a plant rosin. Plant rosin is typically obtainable from a plant's oleo-resin, which is may be exuded or otherwise derived from a pine tree. The oleo-resin may be distilled to remove volatile terpenes, and the solid material left behind is the plant rosin.

Plant rosin may be solid at room temperature. The solid rosin may be relatively translucent and/or glass-like. The plant rosin material may have a color ranging, for example from faint yellow to a darker brown color, or even black.

Plant rosin is typically a mixture of compounds and is primarily composed of resin acids (also called rosin acids). The plant rosin may comprise at least about 75%, or at least about 80%, or at least about 85%, or at least about 90%, or at least about 95%, by weight of the plant rosin, of resin acids. The plant rosin may comprise from about 75% to about 97%, or from about 80% to about 96%, or from about 85% to about 95%, or from about 90% to about 95%, by weight of the plant rosin, of resin acids. The remaining material may be non-acidic material.

Resin acids are typically monocarboxylic acids having three fused rings. Resin acids may be tricyclic diterpene monocarboxylic acids, for example with a molecular formula of $C_{19}H_{29}COOH$. Resin acids may include abietic-type acids, pimaric-type acids, plicatic acid, or mixtures thereof. The double bonds in abietic-type acids are typically conjugated, whereas the double bonds in pimaric-type acids are not typically conjugated.

Abietic-type acids may include abietic acid, neoabietic acid, dehydroabietic acid, palustric acid, levopimaric acid, or mixtures thereof. Pimaric-type acids may include pimaric acid, isopimaric acid, sandaracopimiaric acid, or mixtures thereof. Structures for these illustrative resin acids are provided below in Table A.

TABLE A

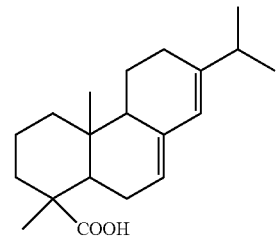

Abietic acid

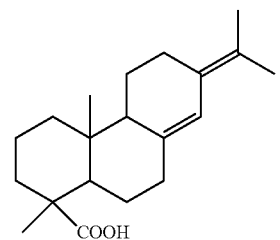

Neoabietic acid

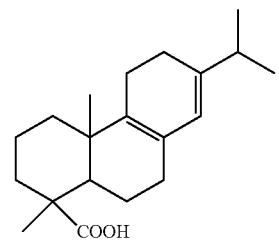

Palustric acid

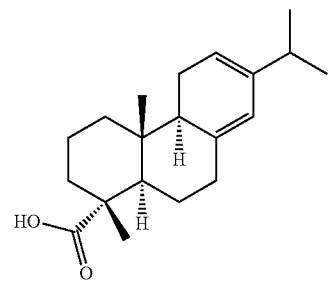

Levopimaric acid

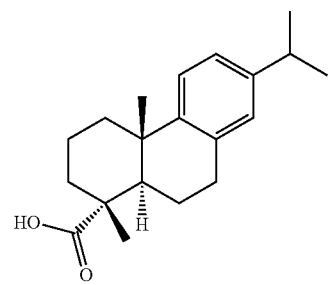

Dihydroabietic acid

TABLE A-continued

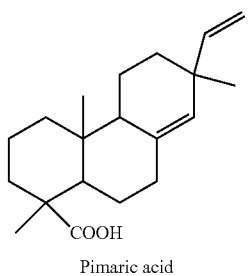 [SMILES: C=CC1(C)C=C2CCC3C(C)(C(=O)O)CCCC3(C)C2CC1]

Pimaric acid

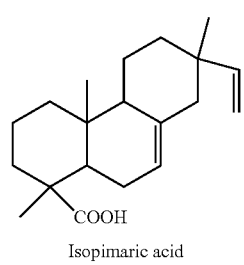 [SMILES: C=CC1(C)CCC2C(=CCC3C(C)(C(=O)O)CCCC23C)C1]

Isopimaric acid

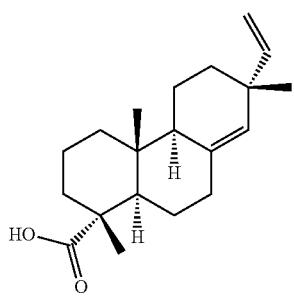

Sandaracopimiaric acid

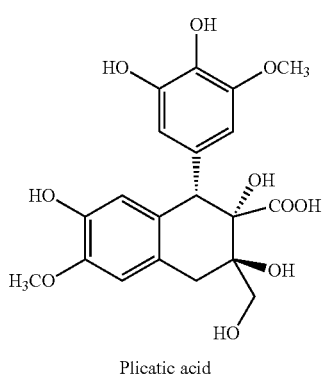 [SMILES: COc1cc2c(cc1O)[C@H](c1cc(O)c(O)c(OC)c1)[C@@](O)(C(=O)O)[C@](O)(CO)C2]

Plicatic acid

The plant rosin may comprise an abietic-type acid, preferably abietic acid. Abietic acid has the empirical formula $C_{19}H_{29}COOH$ and is also known as abietinic acid or sylvic acid. Abietic-type acids are typically the major component of a plant rosin. The plant rosin may comprise at least 50%, or at least 60%, or at least 70%, or at least 80%, or at least 85%, by weight of the plant rosin, of an abietic-type acid, preferably abietic acid.

Plant rosins may be classified depending on the source where it is obtained. For example, plant rosins of the present disclosure may be classified as (and may comprise) gum rosin, wood rosin, tall oil rosin, or a mixture thereof. Gum rosin may be derived from a resin extrudate of a tree or other plant and may be harvested by tapping or wounding the tree and then collecting and processing the extrudate. Wood rosin may be derived from materials that are harvested from pine tree stumps, for example through solvent extraction and/or distillation. Tall oil rosin is a by-product of the distillation of crude tall oil during the Kraft process of wood pulp manufacture when pulping pine trees.

Suitable plant rosins may be obtained, for example, from a variety of pine species, such as *Pinus massoniana* (Masson's pine), *P. elliotti* (slash pine), *P. palustris* (longleaf pine), *P. taeda* (loblolly pine), *P. oocarpa* (Mexican yellow pine), *P. leiophylla* (Chihuahua pine), *P. devoniana* (pino lacio, or Michoacan pine), *P. montezumae* (Montezuma pine), *P. pinaster* (maritime pine), *P. sylvestris* (Scots pine), *P. halepensis* (Aleppo pine), *P. insularis* (Benguet pine), *P. kesiya* (Khasi pine), *P. strobus* (Eastern white pine), or mixtures thereof.

B. Plant Rosin Derivatives

The plant rosin material of the present disclosure may comprise a plant rosin derivative. A plant rosin derivative may be made by chemically modifying a plant rosin material, such as a rosin acid such as abietic acid. Such derivatives may be produced by esterification, hydrogenation, dimerization, polymerization, saponification, or mixtures thereof. Thus, the plant rosin derivative may comprise a rosin ester, a hydrogenated rosin, a hydrogenated rosin ester, a dimerized rosin, a polymerized rosin, or mixtures thereof.

The plant rosin material may be a plant rosin ester. A plant rosin ester may be the reaction product of a plant rosin (e.g., a rosin acid) and an alcohol. A sample condensation reaction between three abietic acid molecules and one glycerol molecule is shown below, resulting in a rosin ester.

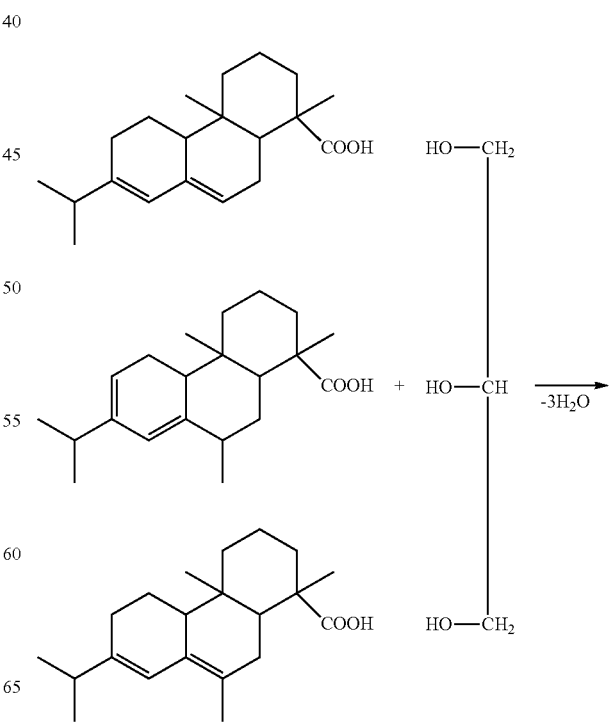

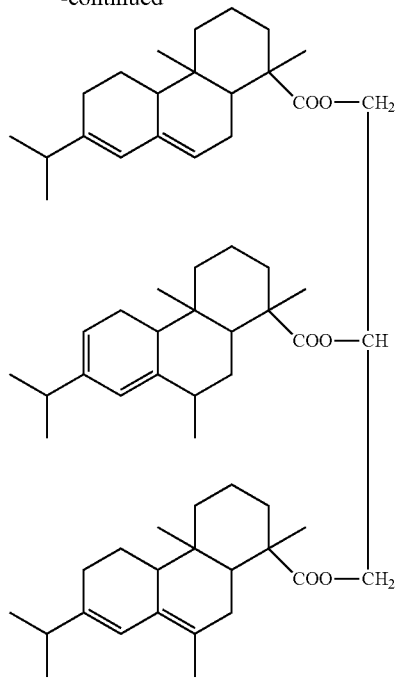

The alcohol in the esterification reaction may be a mono-alcohol, a diol, or a polyol, preferably a diol or a polyol. Suitable mono-alcohols may include methanol, which when reacted with a rosin acid can form a rosin methyl ester. A suitable diol with two hydroxyl groups can include triethylene glycol. The alcohol may be a polyol that comprises three or more hydroxyl groups. Suitable polyols may include a total of three hydroxyl groups (e.g., glycerol), a total of four hydroxyl groups (e.g., pentaerythritol), or a total of six hydroxyl groups (e.g., sorbitol or mannitol). Preferred polyols include glycerol, pentaerythritol, and mixtures thereof.

The alcohol in the esterification reaction may comprise between 1 and 10 carbon atoms, preferably between 1 and 7, more preferably from between 1 and 6, even more preferably between 1 and 5, even more preferably between 3 and 5 carbon atoms. It may be preferred that the alcohol in the esterification reaction comprises at least 2 carbon atoms, preferably from 2 to 10, more preferably from 2 to 6, even more preferably from 2 to 5 carbon atoms. It may be preferred that the rosin ester is not a methyl ester.

The alcohol used in the esterification reaction may have a relatively low molecular weight. For example, the alcohol may have a molecular weight of from about to about 32 daltons to about 300 daltons, preferably from about 32 daltons to about 200 daltons, more preferably from about 32 daltons to about 150 daltons, even more preferably from about 90 daltons to about 150 daltons. Without wishing to be bound by theory, it is believed that a rosin ester formed from a lower-molecular-weight alcohol is likely to be characterized by a relatively lower softening point and/or a lower acid value compared to a rosin ester formed from a relatively higher-molecular-weight alcohol, thereby leading to better processability and/or performance.

The alcohol used in the esterification reaction may be glycerol or pentaerythritol. Thus, the plant rosin derivative may be a glyceryl rosin ester, a pentaerythrityl rosin ester, or a mixture thereof.

The plant rosin derivative may be a hydrogenated rosin. Given that many plant rosin compounds (e.g., rosin acids) are unsaturated, they tend to be oxidatively unstable and may undergo color changes upon storage. Hydrogenation can help to stabilize the rosins and reduce undesirable color change. Furthermore, hydrogenated rosins tend to have lighter colors than the parent rosin, providing more formulation and aesthetic flexibility.

The plant rosins and/or rosin acids may be partially or fully hydrogenated. Below is a sample reaction for the partial and full hydrogenation of abietic acid.

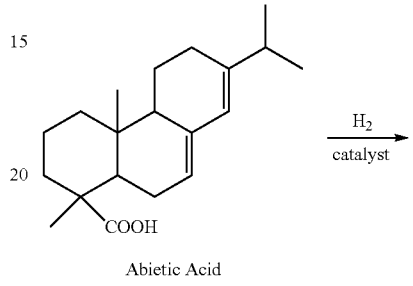

Abietic Acid

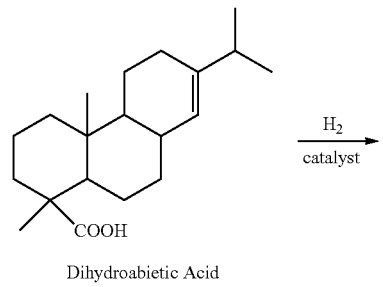

Dihydroabietic Acid

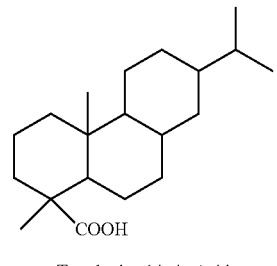

Tetrahydroabietic Acid

The treatment composition may comprise a plant rosin material is at least partially hydrogenated, preferably fully hydrogenated.

The plant rosin derivative may be both hydrogenated and esterified. For example, the plant rosin derivative may be a hydrogenated methyl ester or a hydrogenated glyceryl ester.

The plant rosin derivative may be a dimerized plant rosin. Dimerization may be useful for increasing the softening point and/or stability of a rosin acid. A sample dimerization reaction of abietic acid is shown below.

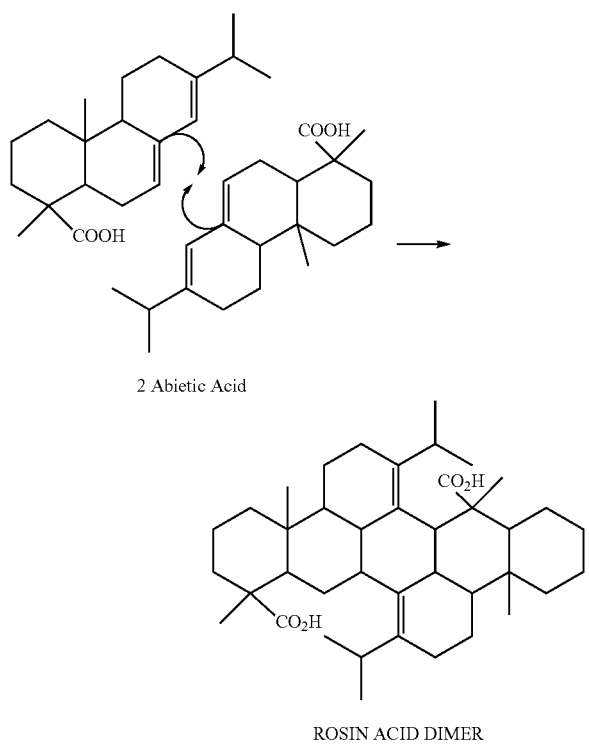

2 Abietic Acid

ROSIN ACID DIMER

As it is difficult or even impossible to completely dimerize a sample of rosins, rosin dimers are often present with undimerized rosin acids. Dimerized rosin acids may be further esterified.

A plant rosin derivative may dimerized through ions such as $Zi^{2+}$ or $Ca^{2+}$. For example, zinc resinates are plant rosin derivatives where two abietic acid compounds are bound to a zinc ion.

The plant rosin derivative may be a rosin-based polymer. As used here, in rosin-based polymer is intended to include compounds comprising rosin-based oligomers, including three or more monomeric units derived from rosin acids. The polymer may be a main-chain polymer or a side-chain polymer.

The plant rosin derivative may be a rosin soap, where a rosin acid is reacted with an alkali metal hydroxide (e.g., NaOH or KOH) or an alkaline earth metal hydroxide (e.g., $Ca(OH)_2$). More broadly, the plant rosin derivative may be the salt of a rosin acid.

The plant rosin derivative may be a functionalized plant rosin. In other word, the plant rosin may be functionalized, where one or more functional groups are added to the plant rosin.

A plant rosin derivative may include the product of a Diels-Alder reaction, such as the reaction product of a rosin acid and maleic anhydride; such reaction products may be polymerized.

A plant rosin derivative may include phenolic rosins, where a rosin is reacted with a phenol. A plant rosin derivative may include a rosin alcohol, wherein one or more of the carboxyl groups of the rosin acid are converted to hydroxyl groups.

Commercially available plant rosin derivatives that are suitable for the presently disclosed compositions and processes may include those disclosed in Example 1 of the Examples section below.

Fragrance Material

The treatment compositions include a fragrance material, which may comprise one or more perfume raw materials. It has been found that perfume raw materials that are characterized by particular structures or chemistries work particularly well in combination with the plant rosin materials described herein, resulting in improved freshness performance.

The term "perfume raw material" (or "PRM") as used herein refers to compounds having a molecular weight of at least about 100 g/mol and which are useful in imparting an odor, fragrance, essence, or scent, either alone or with other perfume raw materials. Typical PRMs comprise inter alia alcohols, ketones, aldehydes, esters, ethers, nitrites, and alkenes, such as terpene. A listing of common PRMs can be found in various reference sources, for example, "Perfume and Flavor Chemicals", Vols. I and II; Steffen Arctander Allured Pub. Co. (1994) and "Perfumes: Art, Science and Technology", Miller, P. M. and Lamparsky, D., Blackie Academic and Professional (1994).

A fragrance material may include a plurality of perfume raw materials, such as at least five, or at least ten, or at least fifteen, or even at least twenty; use of a variety of PRMs in a fragrance material can provide an improved scent experience, such as a more desirable character.

The fragrance material may contain a maximum number of PRMs, which can help to reduce processing complexity and/or minimize detrimental interactions; for example, the fragrance material may contain up to fifty, or up to forty, or up to thirty, or up to twenty-five, or up to twenty, or up to fifteen PRMs.

In particular, the fragrance materials of the present disclosure may include perfume raw materials that are characterized by certain chemical or structural moieties. For example, the fragrance material may comprise one or more perfume raw materials that comprise a moiety selected from the group consisting of a cycloalkane moiety, a cycloalkene moiety, a branched alkane moiety, and combinations thereof. Without wishing to be bound by theory, it is believed that structural similarities between these types of PRMs and plant rosin materials (e.g., abietic-acid-type materials) can facilitate chemical and/or physical associations between the materials and thereby result in improved freshness performance, for example due to improved deposition of the PRMs. It may further be preferred that the one or more PRMs comprise an aldehyde moiety, which can contribute to desirable olfactory experiences as well as advantageous interactions with the plant rosin material.

The one or more perfume raw materials may comprise a cycloalkane moiety, preferably a cycloalkane moiety comprising a ring structure having from five to seven carbons, preferably from five to six carbons, that form the ring structure. The one or more perfume raw materials may comprise a cycloalkene moiety, preferably a cycloalkene moiety comprising a ring structure having from five to seven carbons, preferably from five to six carbons, that form the ring structure. The one or more perfume raw materials may comprise a branched alkane moiety, preferably a branched alkane moiety comprising from one to four carbon atoms, preferably from two to three carbon atoms. It is believed that moieties of the indicated sizes are likely to provide better associates with the plant rosin material compared to differently sized moieties.

The one or more perfume raw materials may comprise at least two moieties selected from the group consisting of a cycloalkane moiety, a cycloalkene moiety, and a branched alkane moiety.

The one or more perfume raw materials may be present in an amount of from about 25% to about 100%, preferably from about 50% to about 95%, more preferably from about 60% to about 90%, even more preferably from about 70% to about 80%, by weight of the fragrance materials.

Preferred perfume raw materials (including CAS numbers) may be selected from the group consisting of: methyl nonyl acetaldehyde (110-41-8); eucalyptol (470-82-6); rose oxide L (3033-23-6); damascenone total 937459 (23696-85-7); orange oil cold pressed (138-86-3); ionone gamma methyl (127-51-5); dimethyl benzyl carbinyl acetate (151-05-3); methyl iso butenyl tetrahydro pyran (16409-43-1); p.t. bucinal (80-54-6); veloutone (65443-14-3); alpha terpineol supra (98-55-5); tetra hydro muguol (18479-57-7); allyl cyclohexane propionate (2705-87-5); citronellol (106-22-9); peonile (10461-98-0); cashmeran (33704-61-9); fructalate 943871 (72903-27-6); delta damascone (57378-68-4); dihydro terpinyl acetate (53767-93-4); iso bornyl acetate (125-12-2); ionone gamma methyl (127-51-5); verdox (88-41-5); aphermate (25225-08-5); Amber Xtreme (476332-65-7); galbascone (56973-85-4); tetra hydro linalool (78-69-3); orange flower ether (14576-08-0); frutene (17511-60-3); iso E super (54464-57-2); cymal (103-95-7); ligustral-2 (27939-60-2); ligustral-1 (68039-49-6); methyl dihydro jasmonate (24851-98-7); cedryl methyl ether (19870-74-7); adoxal (141-13-9); dimethyl benzyl carbinyl butyrate (10094-34-5); dupical (30168-23-1); flor acetate (5413-60-5); undecavertol (81782-77-6); methyl nonyl acetaldehyde (110-41-8); habanolide (111879-80-2); mintonat (67859-96-5); heliotropin (120-57-0); vertenex (32210-23-4); helvetolide (141773-73-1); ethanone, 1-(1,2,3,5,6,7,8,8a-octahydro-2,3,8,8-tetramethyl-2-naphthalenyl)-(68155-66-8); alpha-pinyl isobutyraldehyde (33885-52-8); sandalore (65113-99-7); galaxolide (1222-05-5); isocyclocitral (1335-66-6); cyclohexane, 3-ethoxy-1,1,5-trimethyl-(67583-77-1); jasmacyclene (5413-60-5); 4-tertiary butyl cyclohexyl acetate (32210-23-4); methyl cedrylone (32388-55-9); hexamethylindanopyran (1222-05-5); nectaryl (95962-14-4); cyclabute (67634-20-2); cetalox (3738-00-9); pyranol (63500-71-0); iso gamma super (68155-66-8); orange terpenes (5989-27-5); laevo menthol (2216-51-5); laevo trisandol (28219-61-6); florhydral (125109-85-5); and mixtures thereof. It is believed that these PRMs are illustrative examples of well-perfuming PRMs when used in combination with the plant rosin materials according to the present disclosure.

Based on the data and/or molecular descriptors presented below, it is believed that the following PRMs may be particularly useful: methyl nonyl acetaldehyde (110-41-8); eucalyptol (470-82-6); rose oxide L (3033-23-6); damascenone total 937459 (23696-85-7); orange oil cold pressed (138-86-3); ionone gamma methyl (127-51-5); dimethyl benzyl carbinyl acetate (151-05-3); methyl iso butenyl tetrahydro pyran (16409-43-1); p.t. bucinal (80-54-6); tetra hydro muguol (18479-57-7); dihydro terpinyl acetate (53767-93-4); iso bornyl acetate (125-12-2); ionone gamma methyl (127-51-5); verdox (88-41-5); aphermate (25225-08-5); Amber Xtreme (476332-65-7); galbascone (56973-85-4); tetra hydro linalool (78-69-3); orange flower ether (14576-08-0); frutene (17511-60-3); iso E super (54464-57-2); cymal (103-95-7); ligustral-2 (27939-60-2); ligustral-1 (68039-49-6); methyl dihydro jasmonate (24851-98-7); cedryl methyl ether (19870-74-7); adoxal (141-13-9); dimethyl benzyl carbinyl butyrate (10094-34-5); dupical (30168-23-1); flor acetate (5413-60-5); undecavertol (81782-77-6); methyl nonyl acetaldehyde (110-41-8); habanolide (111879-80-2); mintonat (67859-96-5); vertenex (32210-23-4); helvetolide (141773-73-1); ethanone, 1-(1,2,3,5,6,7,8,8a-octahydro-2,3,8,8-tetramethyl-2-naphthalenyl)-(68155-66-8); alpha-pinyl isobutyraldehyde (33885-52-8); sandalore (65113-99-7); 4-tertiary butyl cyclohexyl acetate (32210-23-4); pyranol (63500-71-0); iso gamma super (68155-66-8); or mixtures thereof.

The plant rosin material and at least a portion of the fragrance material ("co-located portion") are co-located in one or more particles. Without wishing to be bound by theory, it is believed that in such a configuration, the co-located portion of the fragrance material is encapsulated by and/or embedded in a plant rosin matrix. Preferably, the particles have a volume-weighted median particle size of from about 10 microns to about 400 microns, or from about 15 microns to about 300 microns, or from about 20 microns to about 250 microns, or from about 25 microns to about 200 microns, or from about 30 microns to about 150 microns, or from about 35 to about 125 microns, preferably from about 40 to about 100 microns, more preferably from about 50 to about 90 microns. It is believed that such particles facilitate improved freshness performance, for example, by facilitating improved PRM deposition onto a target surface.

The co-located portion of the fragrance material may comprise at least 50%, by weight of the co-located portion of the fragrance material, of the one or more perfume raw materials that comprise the moiety selected from the group consisting of a cycloalkane moiety, a cycloalkene moiety, a branched alkane moiety, and combinations thereof. As mentioned above, it is believed that such PRMs form advantageous associations with the plant rosin material.

It may be that the co-located portion of the fragrance material contains relatively limited amounts, if any, of less-preferred PRMs, such as PRMs that are not characterized by the structural moieties described above. It is believed that such PRMs generally do not associate as efficiently with the plant rosin material and therefore do not deposit as efficiently as the preferred PRMs; that being said, such PRMs may still be present in order to provide a more complete freshness experience. For example, it may be that the co-located portion of the fragrance material comprises no more than 50%, preferably no more than 30%, more preferably no more than 25%, by weight of the co-located portion of the fragrance material, of perfume raw materials that comprise a moiety selected from the group consisting of a C4-C24 linear alkane moiety, an aromatic moiety, and combinations thereof. The co-located portion of the fragrance materials may comprise from about 1% to about 50%, or from about 5% to about 30%, or from about 10% to about 25%, by weight of the co-located portion of the fragrance material, of such (less-preferred) PRMs.

The treatment composition may comprise free fragrance material, which for the purposes of this disclosure means that such fragrance material is not co-located with plant rosin material and is not otherwise encapsulated. Free fragrance material is instead found unbound, unassociated, and/or unencapsulated in the matrix, for example in a liquid matrix, of the treatment composition. Typically, free fragrance material is added as an input that is separate from the plant rosin material.

As described above, certain PRMs are less likely to associate with the plant rosin material. Therefore, in order to formulate a more complete, well-rounded freshness experience, it may be preferred to include such PRMs as free fragrance material. The free fragrance material may comprise one or more perfume raw materials that comprise a moiety selected from the group consisting of a C4-C24 linear alkane moiety, an aromatic moiety, and combinations thereof. The free fragrance material may comprise at least about 25%, preferably at least about 50%, by weight of the free fragrance material, of such one or more perfume raw materials.

The fragrance materials of the present disclosure may include perfume raw materials that can be described by certain molecular descriptors. The molecular descriptors described herein relate to certain aspects of a PRM's molecular structure. Without being bound by theory, it is believed that certain structures, e.g. certain three-dimensional structures, favor strong molecular interactions with the terpene structure present in the plant rosin itself, resulting in improved partitioning and more compatible, and thus more preferred, PRMs. The molecular descriptors described herein are useful in describing the molecular structures, thus are useful in predicting which PRMs will be preferred. Because the molecular descriptors can be determined by use of a computer program, lab resources may be conserved when predicting/determining which PRMs are most likely to work well with the plant rosin materials to provide efficient perfume delivery.

For example, SsssCH, Gmin and dxp10 are molecular descriptors that may be useful in the present compositions and processes. The values and descriptions of SsssCH, Gmin and dxp10 can be found in literature and in commercially available software programs. Specifically, selected descriptors as used herein are computed from software programs winMolconn version 1.1.2.1 (available from Hall Associates Consulting of Quincy, MA), used according to the manufacturer's instructions. Structures are prepared using a 2D connection table (SDF format or SMILES). The molecular descriptor labels used in the model test method computations are the same labels reported by the winMolconn, and their descriptions and definitions can be found listed in the winMolconn documentations. The descriptors relate to the structure of the PRMs, such as the spatial conformation of the molecule and with the positioning of electronegative groups within the molecule. Each molecular descriptor is described in more detail below.

SsssCH is sum of all atom level electrotopological state (E-state) values for all >CH-carbon atoms where a carbon is single-bonded to one hydrogen and three non-hydrogens. This value will increase as a result of increased branched carbons in the molecule.

dxp10 is the simple difference chi path 10 topological index. This value will be size-dependent and also polarity-dependent. Larger molecules will have larger positive values of dxp10, but larger molecules with more heteroatoms will have a more negative value for dxp10.

Gmin is the lowest atom level E-state encoding the possible site of nucleophilic attack. While nucleophilic attack is not expected to be part of the mechanism to explain why a rosin/PRM pairing may be more efficient than PRM alone, the descriptor Gmin may reflect more on the relative charge distribution in a molecule, which can be important for explaining properties like water solubility.

In addition to the winMolconn documentation, the following references can provide more information about molecular structures and properties related to molecular descriptors: L. Hall, B. Mohney, and L. Kier, "The Electrotopological State: Structure Information at the Atomic Level for Molecular Graphs," *J. Chem. Inf. Comput. Sci.* 1991, 31, 76-82; L. Hall and L. Kier, "The Molecular Connectivity Chi Indexes and Kappa Shape Indexes in Structure-Property Modeling," *Reviews in Computational Chemistry*, 1991, Vol. 2, 367-422; R. Todeschini and V. Consonni, *Molecular Descriptors for Chemoinformatics—Volume II: Appendices, References*, 2009, Wiley-VCH.

The fragrance material may comprise one or more perfume raw materials characterized by one of the following parameters, as reported by software program winMolconn version 1.1.2.1, available from Hall Associates Consulting of Quincy, MA: (a) a SsssCH value of $\geq 0.681852$, preferably additionally characterized by a Gmin $<-0.10643$; or (b) a SsssCH value of $<0.681852$ and a dxp10 value of $<-0.00709584$. The fragrance material may contain more than one perfume raw material characterized by (a), more than one perfume raw material characterized by (b), or a combination of materials perfume raw materials where one or more are characterized by (a) and one or more are characterized by (b). Typically, more than one type of perfume raw material can provide a richer olfactory experience.

The preferred boundaries for each molecular descriptor have been computed based on statistical analysis and modelling of experimental data. In particular, decision tree algorithms have been used to compute the boundaries of each descriptor and classify certain structures into particular populations. It has even been found that the decision tree algorithm and statistical analysis of experimentally derived data can be used to predict performance efficiencies of the rosin/perfume system compared to perfume alone in certain treatment compositions at certain touchpoints.

Premix

The fragrance material may be combined with the plant rosin material in a premix, which may be added to a base composition to make the treatment compositions of the present disclosure. The base composition may comprise an adjunct ingredient, as described in more detail below. Thus, the treatment composition of the present disclosure may comprise a premix, where the premix comprises plant rosin material and one or more benefit agents. The treatment may be formed by a process comprising adding a premix to a base composition, where the premix comprises the plant rosin material and the fragrance material, and where the base composition comprises the adjunct ingredient.

The premix may comprise from about 1% to about 99%, by weight of the premix, of the plant rosin material. The premix may comprise from about 1% to about 99%, by weight of the premix, of the fragrance, preferably of the one or more PRMs described above. The premix may comprise the plant rosin material and the fragrance material (preferably the one or more PRMs described above) in a weight ratio of from about 1:99 to about 99:1, preferably from about 5:95 to about 95:5, more preferably from about 10:90 to about 90:10, more preferably from about 20:80 to about 80:20, more preferably from about 30:70 to about 80:20, more preferably from about 40:60 to about 80:20. It is believed that the performance benefit increases with higher plant rosin:fragrance (or rosin:PRM) weight ratios.

The premix may comprise an emulsifying agent. The premix may comprise from about 1% to about 95%, or from about 5% to about 95%, preferably from about 5% to about 40% by weight of the premix, of the emulsifying agent. The premix may comprise the plant rosin material and the emulsifying agent in a weight ratio of from about 5:95 to about 95:5. The premix may comprise the fragrance material and the emulsifying agent in a weight ratio of from about 5:95 to about 95:5. Suitable emulsifying agents may include surfactants, amphiphilic polymers, or mixtures thereof.

Suitable surfactants may include nonionic surfactants, anionic surfactants, or mixtures thereof, preferably nonionic surfactants. Suitable nonionic surfactants may include alkoxylated surfactants, pyrrolidone-based surfactants (including alkyl pyrrolidones, preferably C12-alkyl pyrrolidones), alkyl polyglycosides, and mixture thereof. Preferable HLB value of the nonionic surfactant is from 3 to 12.5. Suitable commercially available nonionic surfactants may include Lutensol™ XP 40 (ex BASF), Lutensol™ XP 70 (ex BASF), Plurafac™ LF 224 (BASF), Plurafac™ LF 401 (BASF), Ecosurf™ EH 9 (DOW), Neodol™ surfactant (SHELL), Dobanol™ surfactants (SHELL), Surfadone™ LP-300 (ASHLAND, Planteren™ APG 600, or mixtures thereof.

Suitable amphiphilic polymers may include graft copolymers, such as poly(ethylene glycol)-poly(vinyl acetate) graft copolymer, polyvinyl caprolactam-polyvinyl acetate-polyethylene glycol graft copolymer, or mixtures thereof. Commercially available graft copolymers may include Sokalon® HP 22 or Soluplus®, both available from BASF.

The premix may be made by heating the plant rosin material. The plant rosin material may be heated to a temperature equal to or greater than the softening point of the plant rosin material. The premix may be made by combining the heated plant rosin material with the fragrance material, and mixing.

In order to favor the homogeneity of the premix, the mixing may take place in a heated oil bath set at a temperature equal to the softening point of the plant rosin material. As the samples become homogenous, the temperature can be progressively reduced, which helps to lower the risk of loss of volatile materials (e.g., evaporation of volatile PRMs).

A processing aid, for example an emulsifying agent as described above, can be added at any suitable point. Preferably, the emulsifying agent, if any, is combined with the plant rosin material prior to adding the fragrance material. It is believed that this order of addition improves the ease of homogenization of the mixture.

As an additional or alternative step to heating, the plant rosin material may be grinded to small particles and mixed with the benefit agent.

Once made, the premix may be stored at ambient temperatures. That being said, when using the premix to make a final product composition, the premix may be heated, for example heated to around 60° C., before being injected in the finished product or otherwise combined with a base composition. This heating step is most likely to be helpful when the premix is characterized by a relatively high rosin:fragrance material (or rosin:PRM) weight ratio, such as greater than 50:50. When the premix comprises a non-ionic surfactant, for example as an emulsifying agent, the heating step may not be required.

Adjunct Ingredients

The treatment compositions of the present disclosure may further include an adjunct ingredient in addition to the particles of the present disclosure. The adjuncts may be suitable for delivering a treatment benefit to a target surface, such as a fabric or other textile. Adjuncts ingredients, as used herein, may also include agents that facilitate chemical or physical stability in the treatment compositions, such as buffers, structurants/thickeners, and/or carriers.

The adjunct ingredient(s) may be present in the composition at levels suitable for the intended use of the composition. Typical usage levels range from as low as 0.001% by weight of composition for adjuncts such as optical brighteners to 50% by weight of composition for builders.

The adjunct ingredient may include an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, structure elasticizing agents, fabric softeners, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof. The compositions of the present disclosure may include, among other things, an amine, a surfactant system, a conditioning agent, a water-binding agent, a sulfite, a structurant, organic solvent, free perfume, a perfume delivery system, or mixtures thereof. Several of these adjuncts are described in more detail below.

The consumer product adjunct may comprise a surfactant system, conditioning actives, or combinations thereof. Preferably, the surfactant system comprises anionic surfactant, nonionic surfactant, cationic surfactant, and/or zwitterionic surfactant. Preferably, the fabric softening agents comprise a quaternary ammonium compound, silicone compounds, or both.

Liquid consumer product compositions according to the present disclosure may include a surfactant system. The surfactant system may consist of one type of surfactant. The surfactant system may include more than one surfactant.

The compositions of the present disclosure may include from about 20% to about 75%, or from about 25% to about 70%, or from about 30% to about 50%, by weight of the composition, of a surfactant system. Compositions of the present disclosure may include less than 20%, or less than 10%, or less than 5%, or less than 3%, by weight of the composition, of a surfactant system.

The surfactant system may include anionic surfactant, nonionic surfactant, zwitterionic surfactant, cationic surfactant, amphoteric surfactant, or combinations thereof. The surfactant system may include linear alkyl benzene sulfonate, alkyl ethoxylated sulfate, alkyl sulfate, nonionic surfactant such as ethoxylated alcohol, amine oxide, or mixtures thereof. The surfactants may be, at least in part, derived from natural sources, such as natural feedstock alcohols.

Suitable anionic surfactants may include any conventional anionic surfactant. This may include a sulfate detersive surfactant, for e.g., alkoxylated and/or non-alkoxylated alkyl sulfate materials, and/or sulfonic detersive surfactants, e.g., alkyl benzene sulfonates. The anionic surfactants may be linear, branched, or combinations thereof. Preferred surfactants include linear alkyl benzene sulfonate (LAS), alkyl ethoxylated sulfate (AES) including sodium laureth sulfate (SLES), alkyl sulfates (AS) including sodium lauryl sulfate (SLS), or mixtures thereof. Other suitable anionic surfactants include branched modified alkyl benzene sulfonates (MLAS), methyl ester sulfonates (MES), and/or alkyl ethoxylated carboxylates (AEC). The anionic surfactants may be present in acid form, salt form, or mixtures thereof. The anionic surfactants may be neutralized, in part or in whole, for example, by an alkali metal (e.g., sodium) or an amine (e.g., monoethanolamine). In certain treatment compositions, for example, those that include a cationic material such as a fabric conditioning agent, it may be desirable to limit the amount of anionic surfactant present; for example, the treatment composition may comprise less than 5%, or less than 3%, or less than 1%, or less than 0.1%, or even 0%, by weight of the treatment composition, of anionic surfactant.

The surfactant system may include nonionic surfactant. Suitable nonionic surfactants include alkoxylated fatty alcohols, such as ethoxylated fatty alcohols. Other suitable nonionic surfactants include alkoxylated alkyl phenols, alkyl phenol condensates, mid-chain branched alcohols, mid-chain branched alkyl alkoxylates, alkylpolysaccharides (e.g., alkylpolyglycosides), polyhydroxy fatty acid amides, ether capped poly(oxyalkylated) alcohol surfactants, and mixtures thereof. The alkoxylate units may be ethyleneoxy units, propyleneoxy units, or mixtures thereof. The nonionic surfactants may be linear, branched (e.g., mid-chain branched), or a combination thereof. Specific nonionic surfactants may include alcohols having an average of from about 12 to about 16 carbons, and an average of from about 3 to about 9 ethoxy groups, such as C12-C14 EO7 nonionic surfactant.

Suitable zwitterionic surfactants may include any conventional zwitterionic surfactant, such as betaines, including alkyl dimethyl betaine and cocodimethyl amidopropyl betaine, $C_8$ to $C_{18}$ (for example from $C_{12}$ to $C_{18}$) amine oxides (e.g., $C_{12-14}$ dimethyl amine oxide), and/or sulfo and hydroxy betaines, such as N-alkyl-N,N-dimethylammino-1-propane sulfonate where the alkyl group can be $C_8$ to $C_{18}$, or from $C_{10}$ to $C_{14}$. The zwitterionic surfactant may include amine oxide.

The compositions of the present disclosure may include a conditioning active. Compositions that contain conditioning actives may provide softness, anti-wrinkle, anti-static, conditioning, anti-stretch, color, and/or appearance benefits. Conditioning actives suitable for compositions of the present disclosure may include quaternary ammonium ester compounds, silicones, non-ester quaternary ammonium compounds, amines, fatty esters, sucrose esters, silicones, dispersible polyolefins, polysaccharides, fatty acids, softening or conditioning oils, polymer latexes, or combinations thereof. Preferably, the treatment composition comprises a conditioning active that comprises a quaternary ammonium ester compound, more preferably a quaternary ammonium ester compound in combination with a silicone.

Conditioning actives may be present at a level of from about 1% to about 99%, by weight of the composition. The composition may include from about 1%, or from about 2%, or from about 3%, to about 99%, or to about 75%, or to about 50%, or to about 40%, or to about 35%, or to about 30%, or to about 25%, or to about 20%, or to about 15%, or to about 10%, by weight of the composition, of conditioning active. The composition may include from about 5% to about 30%, by weight of the composition, of conditioning active.

Liquid treatment compositions according to the present disclosure may include an external structurant. External structurants can provide physical stability to liquid compositions according to the present disclosure, for example by helping to suspend the delivery particles. Structurants, when present, are preferably present in an effective amount that is capable of suspending the particles in the treatment composition. External structurants may include non-polymeric crystalline, hydroxy-functional structurants and/or polymeric structurants.

Non-polymeric crystalline, hydroxyl functional structurants may comprise a crystallizable glyceride, which may be pre-emulsified to aid dispersion into the final detergent composition. Suitable crystallizable glycerides include hydrogenated castor oil or "HCO" or derivatives thereof, provided that it is capable of crystallizing in the liquid detergent composition.

Polymeric structurants may include naturally derived structurants and/or synthetic structurants. Naturally derived polymeric structurants include: hydroxyethyl cellulose, hydrophobically modified hydroxyethyl cellulose, carboxymethyl cellulose, polysaccharide derivatives and mixtures thereof. Suitable polysaccharide derivatives include: pectine, alginate, arabinogalactan (gum Arabic), carrageenan, gellan gum, xanthan gum, guar gum and mixtures thereof. The structurant may comprise cellulosic fibers, for example in the form of microfibrillated cellulose. Cellulose may be derived from bacterial, wood, or other plants such as fruit or sugar beet.

Synthetic polymeric structurants include: polycarboxylates, polyacrylates, hydrophobically modified ethoxylated urethanes, hydrophobically modified non-ionic polyols and mixtures thereof. The polycarboxylate polymer may be a polyacrylate, polymethacrylate or mixtures thereof. The polyacrylate may be a copolymer of unsaturated mono- or di-carbonic acid and $C_1$-$C_{30}$ alkyl ester of the (meth)acrylic acid. Such copolymers are available from Lubrizol Corp. under the tradename Carbopol® Aqua 30.

The compositions of the present disclosure may include solvent, preferably organic solvent, such as a non-amino-functional organic solvent. Suitable organic solvents may include glycerol, ethylene glycol, 1,3 propanediol, 1,2 propanediol, tetramethylene glycol, pentamethylene glycol, hexamethylene glycol, 2,3-butane diol, 1,3 butanediol, diethylene glycol, triethylene glycol, polyethylene glycol, glycerol formal dipropylene glycol, polypropylene glycol, dipropylene glycol n-butyl ether, and mixtures thereof. Organic solvents can provide physical stability benefits, particularly in compact formulations having relatively low water levels. The compositions of the present disclosure may include from about 5% to about 80%, or from about 10% to about 50%, by weight of the composition, of organic solvent.

Treatment compositions according to the present disclosure may include a perfume delivery system. Suitable perfume delivery systems may include core-shell encapsulates, pro-perfumes (such as amine- and/or silicone-based pro-perfumes), and mixtures thereof. Core-shell encapsulates may comprise a core and a shell surrounding the core. The core may comprise a benefit agent such as perfume, and optionally a partitioning modifier such as isopropyl myristate. The shell may comprise a polymer, for example melamine formaldehyde, polyurea, polyvinyl alcohol, polyacrylate, or a polysaccharide. Encapsulates may comprise a coating that can help with deposition, such as a coating comprising a cationic polymer. Suitable encapsulates may be characterized by a volume-weighted median particle size of from about 10 microns to about 100 microns, or from about 10 microns to about 50 microns, or from about 15 microns to about 40 microns. Perfume delivery systems may provide benefits such as improved perfume stability, deposition, and/or longevity, and may be particularly useful for perfume raw materials that do not associate well with the plant rosin materials of the present disclosure.

The compositions of the present disclosure may include additional aesthetic agents, such as those selected from dyes, opacifiers, pearlescent agents, or mixtures thereof.

When the consumer product composition is in the form of a unit dose article, such as a pouch or a sachet, the composition may be encapsulated by a water-soluble film. A water-soluble unit dose article may comprise at least one water-soluble film shaped such that the unit-dose article comprises at least one internal compartment surrounded by the water-soluble film. The at least one compartment comprises the detergent composition.

The unit dose article may comprise more than one compartment, even at least two compartments, or even at least three compartments, or even at least four compartments, or even at least five compartments. The compartments may be arranged in superposed orientation, i.e. one positioned on top of the other. Alternatively, the compartments may be positioned in a side-by-side orientation, i.e. one orientated next to the other. The compartments may even be orientated in a "tire and rim" arrangement, i.e. a first compartment is positioned next to a second compartment, but the first compartment at least partially surrounds the second compartment, but does not completely enclose the second compartment. Alternatively, one compartment may be completely enclosed within another compartment. When one compartment comprises a liquid composition according to the present disclosure, another compartment may comprise a solid, a liquid, or a mixture thereof.

The film of the present invention may be soluble or dispersible in water (e.g., at 20° C.). Preferred film materials include polymeric materials. The film material can, for example, be obtained by casting, blow-moulding, extrusion or blown extrusion of the polymeric material, as known in the art. Preferably, the water-soluble film comprises polyvinyl alcohol polymer or copolymer, preferably a blend of polyvinylalcohol polymers and/or polyvinylalcohol copolymers, preferably selected from sulphonated and carboxylated anionic polyvinylalcohol copolymers especially carboxylated anionic polyvinylalcohol copolymers, most preferably a blend of a polyvinylalcohol homopolymer and a carboxylated anionic polyvinylalcohol copolymer. Suitable films include those supplied by MonoSol, LLC (Indiana) under the trade references M8630, M8900, M8779, and/or M8310. The film may comprise an aversive agent, for example a bittering agent. Prior to be being formed into a unit dose article, the water-soluble film preferably has a thickness of from 20 to 150 microns, preferably 35 to 125 microns, even more preferably 50 to 110 microns, most preferably about 76 microns.

Methods of Making

The present disclosure also relates to processes for making treatment compositions, preferably liquid treatment compositions. The process of making a treatment composition, which may be a consumer product composition, may comprise the step of combining the ingredients (e.g., a plant rosin material, one or more benefit agents, and optionally an adjunct ingredient) as described herein.

The process of making a treatment composition, which may be a liquid, according to the present disclosure may comprise the steps of combining the plant rosin material and the one or more benefit agents as separate ingredients (e.g., without premixing the plant rosin material and the one or more benefit agents) with a liquid base composition, where the liquid base composition comprises an adjunct ingredient.

The process of making a treatment composition according to the present disclosure may include the step of providing a premix. The premix may comprise the plant rosin material and the one or more benefit agents. The premix may be combined with a base composition, preferably a liquid base composition. The liquid base composition may comprise the adjunct ingredient.

The treatment compositions of the present disclosure can be formulated into any suitable form and prepared by any process chosen by the formulator. Liquid materials may be combined in a batch process, in a circulation loop process, and/or by an in-line mixing process. Suitable equipment for use in the processes disclosed herein may include continuous stirred tank reactors, homogenizers, turbine agitators, recirculating pumps, paddle mixers, high shear mixers, static mixers, plough shear mixers, ribbon blenders, vertical axis granulators and drum mixers, both in batch and, where available, in continuous process configurations, spray dryers, and extruders.

The treatment composition may be encapsulated in water-soluble film(s) according to known methods to form a unitized dose article.

Liquid treatment compositions may be placed into an aerosol or other spray container according to known methods.

Methods of Using

The present disclosure also relates to a process of treating a surface, such as a fabric, hair, and/or skin. The process may include the step of contacting a surface with a treatment composition according to the present disclosure.

The contacting step may occur in the presence of water. The processes of the present disclosure may include diluting the compact liquid detergent composition with water to form a treatment liquor, which may contact the surface to be treated. The compact liquid detergent composition may be diluted from 100-fold to 1000-fold, or from 200-fold to 900-fold, or from 300-fold to 800-fold, by water.

The contacting step may occur in the drum of an automatic washing machine. The contacting step may occur as a pretreatment step.

COMBINATIONS

Specifically contemplated combinations of the disclosure are herein described in the following lettered paragraphs. These combinations are intended to be illustrative in nature and are not intended to be limiting.

A. A treatment composition comprising a plant rosin material and a fragrance material, wherein the fragrance material comprises one or more perfume raw materials, wherein the one or more perfume raw materials comprise a moiety selected from the group consisting of a cycloalkane moiety, a cycloalkene moiety, a branched alkane moiety, and combinations thereof.

B. A treatment composition comprising a plant rosin material and a fragrance material, wherein the fragrance material comprises one or more perfume raw materials characterized by one of the following parameters, determined according to the test methods described herein: (a) a SsssCH value of ≥0.681852, preferably additionally characterized by a Gmin <−0.10643; or (b) a SsssCH value of <0.682 and a dxp10 value of <−0.00709584.

C. The treatment composition according to any of paragraphs A or B, wherein the one or more perfume raw materials comprises a cycloalkane moiety, preferably a cycloalkane moiety comprising a ring structure having from five to seven carbons, preferably from five to six carbons, that form the ring structure.

D. The treatment composition according to any of paragraphs A-C, wherein the one or more perfume raw materials comprises a cycloalkene moiety, preferably a cycloalkene moiety comprising a ring structure having from five to seven carbons, preferably from five to six carbons, that form the ring structure.

E. The treatment composition according to any of paragraphs A-D, wherein the one or more perfume raw materials comprises a branched alkane moiety, preferably a branched alkane moiety comprising from one to four carbon atoms, preferably from two to three carbon atoms.

F. The treatment composition according to any of paragraphs A-E, wherein the one or more perfume raw materials comprise at least two of a cycloalkane moiety, a cycloalkene moiety, and a branched alkane moiety.

G. The treatment composition according to any of paragraphs A-F, wherein the one or more perfume raw materials are present in an amount of from about 25% to about 100%, preferably from about 50% to about 95%, more preferably from about 60% to about 90%, even more preferably from about 70% to about 80%, by weight of the fragrance materials.

H. The treatment composition according to any of paragraphs A-G, wherein the one or more perfume raw materials are selected from the group consisting of: methyl nonyl acetaldehyde (CAS #110-41-8); eucalyptol (470-82-6); rose oxide L (3033-23-6); damascenone total 937459 (23696-85-7); orange oil cold pressed (138-86-3); ionone gamma methyl (127-51-5); dimethyl benzyl carbinyl acetate (151-05-3); methyl iso butenyl tetrahydro pyran (16409-43-1); p.t. bucinal (80-54-6); veloutone (65443-14-3); alpha terpineol supra (98-55-5); tetra hydro muguol (18479-57-7); allyl cyclohexane propionate (2705-87-5); citronellol (106-22-9); peonile (10461-98-0); cashmeran (33704-61-9); fructalate 943871 (72903-27-6); delta damascone (57378-68-4); dihydro terpinyl acetate (53767-93-4); iso bornyl acetate (125-12-2); ionone gamma methyl (127-51-5); verdox (88-41-5); aphermate (25225-08-5); Amber Xtreme (476332-65-7); galbascone (56973-85-4); tetra hydro linalool (78-69-3); orange flower ether (14576-08-0); frutene (17511-60-3); iso E super (54464-57-2); cymal (103-95-7); ligustral-2 (27939-60-2); ligustral-1 (68039-49-6); methyl dihydro jasmonate (24851-98-7); cedryl methyl ether (19870-74-7); adoxal (141-13-9); dimethyl benzyl carbinyl butyrate (10094-34-5); dupical (30168-23-1); flor acetate (5413-60-5); undecavertol (81782-77-6); methyl nonyl acetaldehyde (110-41-8); habanolide (111879-80-2); mintonat (67859-96-5); heliotropin (120-57-0); vertenex (32210-23-4); helvetolide (141773-73-1); ethanone, 1-(1,2,3,5,6,7,8,8a-octahydro-2,3,8,8-tetramethyl-2-naphthalenyl)-(68155-66-8); alpha-pinyl isobutyraldehyde (33885-52-8); sandalore (65113-99-7); galaxolide (1222-05-5); isocyclocitral (1335-66-6); cyclohexane, 3-ethoxy-1,1,5-trimethyl-(67583-77-1); jasmacyclene (5413-60-5); 4-tertiary butyl cyclohexyl acetate (32210-23-4); methyl cedrylone (32388-55-9); hexamethylindanopyran (1222-05-5); nectaryl (95962-14-4); cyclabute (67634-20-2); cetalox (3738-00-9); pyranol (63500-71-0); iso gamma super (68155-66-8); orange terpenes (5989-27-5); laevo menthol (2216-51-5); laevo trisandol (28219-61-6); florhydral (125109-85-5); and mixtures thereof; preferably wherein the one or more perfume raw materials are selected from the group consisting of: methyl nonyl acetaldehyde (CAS #110-41-8); eucalyptol (470-82-6); rose oxide L (3033-23-6); damascenone total 937459 (23696-85-7); orange oil cold pressed (138-86-3); ionone gamma methyl (127-51-5); dimethyl benzyl carbinyl acetate (151-05-3); methyl iso butenyl tetrahydro pyran (16409-43-1); p.t. bucinal (80-54-6); tetra hydro muguol (18479-57-7); dihydro terpinyl acetate (53767-93-4); iso bornyl acetate (125-12-2); ionone gamma methyl (127-51-5); verdox (88-41-5); aphermate (25225-08-5); Amber Xtreme (476332-65-7); galbascone (56973-85-4); tetra hydro linalool (78-69-3); orange flower ether (14576-08-0); frutene (17511-60-3); iso E super (54464-57-2); cymal (103-95-7); ligustral-2 (27939-60-2); ligustral-1 (68039-49-6); methyl dihydro jasmonate (24851-98-7); cedryl methyl ether (19870-74-7); adoxal (141-13-9); dimethyl benzyl carbinyl butyrate (10094-34-5); dupical (30168-23-1); flor acetate (5413-60-5); undecavertol (81782-77-6); methyl nonyl acetaldehyde (110-41-8); habanolide (111879-80-2); mintonat (67859-96-5); vertenex (32210-23-4); helvetolide (141773-73-1); ethanone, 1-(1,2,3,5,6,7,8,8a-octahydro-2,3,8,8-tetramethyl-2-naphthalenyl)-(68155-66-8); alpha-pinyl isobutyraldehyde (33885-52-8); sandalore (65113-99-7); 4-tertiary butyl cyclohexyl acetate (32210-23-4); pyranol (63500-71-0); iso gamma super (68155-66-8); or mixtures thereof.

I. The treatment composition according to any of paragraphs A-H, wherein the plant rosin material and at least a portion of the fragrance material ("co-located portion") are co-located in one or more particles, preferably particles having a volume-weighted median particle size of from about 10 microns to about 400 microns, or from about 15 microns to about 300 microns, or from about 20 microns to about 250 microns, or from about 25 microns to about 200 microns, or from about 30 microns to about 150 microns, or from about 35 to about 125 microns, preferably from about 40 to about 100 microns, more preferably from about 50 to about 90 microns.

J. The treatment composition according to any of paragraphs A-J, wherein the co-located portion of the fragrance material comprises at least 50%, by weight of the co-located portion of the fragrance material, of the one or more perfume raw materials that comprise the moiety selected from the group consisting of a cycloalkane moiety, a cycloalkene moiety, a branched alkane moiety, and combinations thereof.

K. The treatment composition according to any of paragraphs I or J, wherein the co-located portion of the fragrance material comprises no more than 50%, preferably no more than 30%, by weight of the co-located portion of the fragrance material, of perfume raw materials that comprise a moiety selected from the group consisting of a C4-C24 linear alkane moiety, an aromatic moiety, and combinations thereof.

L. The treatment composition according to any of paragraphs A-K, wherein the treatment composition further comprises free fragrance material, preferably wherein the free fragrance material comprises one or more perfume raw materials that comprise a moiety selected from the group consisting of a C4-C24 linear alkane moiety, an aromatic moiety, and combinations thereof, more preferably wherein the free fragrance material comprises at least about 25% by weight of the free fragrance material of such one or more perfume raw materials.

M. The treatment composition according to any of paragraphs A-L, wherein the plant rosin material and the fragrance material are premixed together.

N. The treatment composition according to any of paragraphs A-M, wherein the plant rosin material comprises a material selected from the group consisting of gum rosin, wood rosin, tall oil rosin, derivatives thereof, and mixtures thereof, preferably gum rosin, derivatives thereof, and mixtures thereof, more preferably a gum rosin ester.

O. The treatment composition according to any of paragraphs A-N, wherein the plant rosin material is a plant rosin ester, preferably an ester formed from an alcohol having two or more carbon atoms, more preferably where the alcohol is glycerol, pentaerythritol, or a mixture thereof.

P. The treatment composition according to any of paragraphs A-O, wherein the plant rosin material is at least partially hydrogenated, preferably fully hydrogenated.

Q. The treatment composition according to any of paragraphs A-P, wherein the plant rosin material comprises at least 50%, more preferably at least 60%, more preferably at least 70%, more preferably at least 80%, more preferably at least 85%, by weight of the plant rosin material, of an abietic-type acid, a derivative of an abietic-type acid, or a mixture thereof.

R. The treatment composition according to any of paragraphs A-Q, wherein the plant rosin material is characterized by at least one, preferably at least two, more preferably all three, of the following characteristics: a) a softening point of from about 50° C. to about 175° C., preferably from about 60° C. to about 150° C., more preferably from about 75° C. to about 125° C.; b) an acid number of less than about 175, preferably less than about 125, preferably less than about 100, more preferably less than about 75, even more preferably less than about 50, more preferably less than about 25; c) a color grade of from about 1 to about 10, or from about 1 to about 8, as graded on the Gardner Color standard number.

S. The treatment composition according to any of paragraphs A-R, wherein the treatment composition further comprises a treatment adjunct selected from the group consisting of an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof, preferably wherein treatment adjunct comprises a surfactant system, fabric softening agents, or combinations thereof, preferably wherein the surfactant system comprises anionic surfactant, nonionic surfactant, cationic surfactant, and/or zwitterionic surfactant, and/or preferably wherein the fabric softening agents comprise a quaternary ammonium compound, silicone compounds, or both.

T. The treatment composition according to any of paragraphs A-S, wherein the treatment composition is in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof, preferably a liquid composition.

U. The treatment composition according to any of paragraphs A-T, wherein the treatment composition comprises at least 8% water, preferably at least 25% water, more preferably at least 50% water, more preferably at least 60% water, more preferably at least 70% water, more preferably at least 75% water, more preferably at least 80% water, more preferably at least 90% water, by weight of the treatment composition.

V. The treatment composition according to any of paragraphs A-U, wherein the treatment composition is a consumer product composition, preferably a fabric care composition, a hard surface cleaner composition, a dish care composition, a hair care composition, a body cleansing composition, or a mixture thereof, more preferably wherein the fabric care composition is a fabric detergent composition, a fabric conditioning composition, or a mixture thereof.

W. A method of treating a surface, preferably a fabric, the method comprising the step of contacting the surface with the treatment composition according to any of paragraphs A-V, optionally in the presence of water.

TEST METHODS

It is understood that the test methods that are disclosed in the Test Methods Section of the present application should be used to determine the respective values of the parameters of Applicant's claimed subject matter as claimed and described herein.

Test Method for Determining the Logarithm of the Octanol/Water Partition Coefficient (log P)

The value of the log of the Octanol/Water Partition Coefficient (log P) is computed for each PRM in the perfume mixture being tested. The log P of an individual PRM is calculated using the Consensus log P Computational Model, version 14.02 (Linux) available from Advanced Chemistry Development Inc. (ACD/Labs) (Toronto, Canada) to provide the unitless log P value. The ACD/Labs' Consensus log P Computational Model is part of the ACD/Labs model suite.

Softening Point Test Method

If available, the softening point of a plant rosin material as provided by the manufacturer/supplier is to be used.

If not available from the manufacturer/supplier, the softening point is determined according to ASTM E28-18, "Standard Test Methods for Softening Point of Resins Derived from Pine Chemicals," using the version approved Jul. 1, 2018, and published July 2018. More specifically, the Reference Method ("Automated Ring and Ball Softening Point Method") provided therein is to be followed. The method is summarized here.

As used herein (and as described in ASTM E28-18), the softening point is defined as the temperature at which a disk of the sample held with a horizontal ring (brass shouldered ring; 19.8 mm inner ring diameter, 23.0 outer diameter, as indicated in the ASTM method) is forced downward a distance of 25.4 mm (1 in.) under the weight of a steel ball (9.53 mm diameter; mass between 3.45 and 3.55 g) as the sample is heated at 5 C/min in a water, glycerin, silicone oil, ethylene glycol/water, or glycerin/water bath.

Sample Preparation: Select a representative sample of the rosin material to be tested. The sample should include flakes, pastilles, or freshly broken lumps free of oxidized surfaces; avoid inclusion of finely divided material or dust. Melt the sample in a clean container; avoid overheating, and avoid incorporating air bubbles into the sample. The time from the beginning of heating to the pouring of the sample should not exceed 15 minutes. Rest the ring, bottom down, on a metal surface; the ring may be preheated. Pour the melted rosin sample into the ring so as to leave an excess upon cooling. After cooling for at least 30 minutes, remove excess material from the periphery and top of the ring.

Bath Liquid: The selection of the bath liquid will depend on the softening point ("SP") of the rosin material. For SPs between 35 C and 80 C, use water (distilled or deionized, freshly boiled). For SPs between 80 C and 150 C, use USP Glycerin. For SPs above 80 C, use Silicone Oil (Polydimethylsiloxane—200 fluid, 50 cSt, from Dow Corning, Midland, MI). For SPs up to 35 C, use a 50/50 (v/v) mixture of Ethylene Glycol and Distilled Water; the bath should be cooled to −25 C in a precooled freezer or an isopropyl dry-ice bath.

Test: Use a suitable automated ring and ball-softening point instrument with control unit; calibrate according to the manufacturer's instructions. Provide a stir bar to a 600 mL beaker and fill with a bath liquid as provided above, depending on the softening point of the rosin material. Set up the apparatus, ring, ball, test insert, support pins as recommended by the manufacturer's instructions. Verify that the control unit is set for the correct bath liquid.

Heat the bath so that the temperature of the bath liquid is raised uniformly at a rate of 5 C/min. The test is complete when then light beam has been interrupted by the falling ball and material. Record the softening point at the temperature displayed on the unit after the test is completed.

Acid Number Test Method

If available, the acid number of a plant rosin material as provided by the manufacturer/supplier is to be used.

If not available from the manufacturer/supplier, the acid value is determined according to ASTM D465-15 (Reapproved 2020), "Standard Test Methods for Acid Number of Pine Chemical Products Including Tall Oil and Other Related Products," as approved Jun. 1, 2020 and published June, 2020. More specifically, the Referee Method ("Potentiometric Method") provided therein is to be followed. The method is summarized here.

Provide freshly chipped samples of rosin material, which may be further crushed to facilitate weighing and dissolution; pieces with oxidized surfaces, as well as existing rosin dust or powder, should not be used. If a nonhomogenous liquid, place in a closed container with a capillary vent or its equivalent, and heat in a hot water bath; the sample may be agitated during heat, and used after homogenous and well stirred.

Based on the following table, transfer the proscribed amount of sample to a 400 mL tall-form beaker; add the proper amount of solvent I and swirl to dissolve, heating gently if necessary. Add the proper amount of solvent II, if required, and cool to near room temperature. Immerse each electrode of a glass electrode pH meter (calibrated/standardized according to the manufacturer's instructions) in the solution. Stir with a stir bar.

Titrate with a standard alkali solution (a 0.5 N or 0.1 N KOH solution), recording the buret and pH meter readings. Sufficient alkali may be added to bring the pH of the solution to about 8. Add alkali in 1.0 mL portions until the change in pH per increment added amounts to about 0.3 pH unit. Reduct the additions of alkali to 0.1 mL or smaller until the end point has been passed, as indicated by a significant decrease in pH units er 0.1 mL added. Continue the titration with 1.0 mL portions until it becomes apparent that the inflection point has been well defined.

Determine the inflection point (point of maximum change in pH per mL of alkali solution) to the nearest 0.05 mL by plotting the pH readings against the milliliters of alkali used. (For greater accuracy, the chance in pH per mL may be plotted against the pH; the peak corresponds to the inflection point.) The inflection point is considered the end point of the titration.

The acid number of the sample, expressed as milligrams of KOH per gram of sample is calculated as follows, and may be reported to the nearest whole number:

$$\text{Acid Number} = (A \times N \times 56.1)/B$$

where: A=alkali solution (in mL) required for titration of the specimen; N=normality of the alkali solution, and B=specimen weight (in grams).

Color Grade Test Method (Gardner Color)

If available, the color grade (Gardner color) of a plant rosin as provided by the manufacturer/supplier is to be used.

If not available from the manufacturer/supplier, the color grade (Gardner color) is determined according to ASTM D6166-12 (Reapproved 2016), "Standard Test Method for Color of Pine Chemicals and Related Products (Instrumental Determination of Gardner Color)," as approved Dec. 1, 2016, and published December, 2016. The method is summarized here.

The color of a liquid sample is measured using an instrument, such as a Gardner Color Comparator L, 115V (ex. BYK), capable of measuring transmitted color and reporting in Gardner colors (or, less preferred, in a color system that can be converted to Gardner colors by known methods, such as those disclosed in the ASTM D6166-12). The instrument is calibrated according to the manufacturer's instructions.

To prepare the rosin sample for color analysis, a molten sample of the rosin material is introduced to a glass cuvet (10-mm path, unless a different path length is specified by the instrument manufacturer). If the sample is solid, it should comprise freshly broken lumps and be free of dust and finely divided material; the solid should be melted (e.g. in 15 minutes or less, in an oven, sand bath, or oil bath), taking care to avoid overheating and introduction of bubbles. After the molten sample is introduced to the glass cuvet, measurements should be taken while still molten. If the material is cloudy, it should be filtered.

The glass cuvet is inserted into the instrument, and the color is measured by following the manufacturer's instructions.

Flash Point Test Method

If available, the flash point of a plant rosin as provided by the manufacturer/supplier is to be used.

If not available from the manufacturer/supplier, the flash point is determined according to ASTM D92-18, "Standard Test Methods for Flash and Fire Points by Cleveland Open Cup Tester," as approved Jul. 1, 2018, and published July, 2018.

Test Method for Determining Amounts of Major Rosin Acid Isomers

If available, the amounts of the major rosin acid isomers of a plant rosin as provided by the manufacturer/supplier is to be used.

If not available from the manufacturer/supplier, the amounts of the major rosin acid isomers are determined according to ASTM D5974-15, "Standard Test Method for Fatty and Rosin Acids in Tall Oil Fractionation Products by Capillary Gas Chromatography," as approved Jul. 1, 2015, and published August, 2015. The method is summarized here.

This method uses gas chromatography to determine the levels of, for example, rosin acids present in a rosin sample. Prior to chromatographic separation, certain free acids should be converted to more volatile and more stable methyl esters. For rosin acids, this conversion may take place by means of tetramethylammonium hydroxide (TMAH).

To prepare the methyl ester, a rosin sample (if solid, freshly broken to avoid oxidation) is dissolved in 0.5-3.0 mL of a 50:50 ether/methanol mixture (and optionally 2 to 3 drops of toluene), 2 to 3 drops of phenolphthalein indicator solution is added. The mixture is titrated to a pH of 7.9 to 8.1, or to the very first permanent pink color, with a 6% solution of TMAH. If over-titrated, the mixture may be back-titrated with a 5% acetic acid solution (v/v) in methanol. When the solution is injected into the heated injection port of the chromatograph, the tetramethylammonium salts are pyrolyzed to methyl esters.

A gas chromatograph (GC) equipped with a flame ionization detector (FID) is used and operated under the following conditions: Column temperature (oven temperature)—initial, 150 C; hold, 5 min.; ramp, 5 C/min; final 250 C; hold 10 min; injection port temp., 300 C; injection port liner, glass split; detector temp., 325 C; carrier gas, helium; linear gas velocity, 19.5-20.5 cm/s; split ratio, 100 to 1 maximum; detector, FID; hydrogen, 30 mL/min; air, 400 mL/min; makeup gas, 30 mL/min. A high resolution column, preferably 30 m in length, 0.32 mm internal diameter, with a 0.20-μm film thickness of bicyanopropylsiloxane-type liquid, is used.

Prepare calibration standards of myristic acid and high-purity standards of rosin acids that are expected to be present, record the weights, and convert to methyl esters as described above. To prepare the test sample, accurately weigh about 50 mg of sample and about 15 mg of myristic acid in a suitable vial, record the weight, and convert to methyl esters as described above.

Use the calibration standards (injecting 0.5-1.0 μL) to calibrate the GC, recording the retention times and calculating the individual relative response factors. To analyze the test sample, inject 0.5-1.0 μL (diluting the sample with additional solvent if necessary), obtain the peak areas of all of the peaks needed from the chromatogram, and calculate the absolute value of each peak of interest. The relative percent of each rosin acid methyl ester present may be determined by dividing the peak area for the rosin acid methyl ester being determined by the sum of areas of all rosin acid methyl ester peaks.

Fabric Treatment Method

When treating fabrics with a composition according to the present disclosure in the experiments below, the following method is followed unless otherwise indicated. For each treatment, a washing machine (ex Miele) is loaded with about 3 kg of a fabric load. The fabric load comprises about 1065 g knitted cotton fabric and about 1065 g polyester-cotton fabrics (50/50). Additionally, the fabric load comprises twenty terry towel tracers, which weigh together about 870 g.

Before the wash, the machine is cleaned out. In total 4 ethanol wipes are used: one for the first half of the inox drum; another one for the second half of the inox drum; the third wipe for the rubber of the washing machine; the fourth for the washing machine drawer. The washing machine is left open for minimum one minute. Then one washing cycle is run at 95° C.

Prior to the test treatment, the load is preconditioned twice, each time using the 95° C. short cotton cycle with 79 g of unperfumed IEC A Base detergent (ex WFK Testgewebe GmbH), followed by two additional 95° C. washes without detergent.

For the test treatment, the load is washed using a 40° C. short cotton cycle, 1200 rpm spin speed with 79 g IEC A Base detergent, which is added at the start of the wash cycle in the appropriate dispenser. A dosage of 40 ml of the test fabric treatment composition is added in the appropriate dispenser.

The fabrics are either line dried or dried with a tumble-drying machine (Miele Novotronic T490) and analyzed at the desired touchpoint.

Method to Determine Headspace Concentration Above Treated Fabrics

The fabric tracers from the abovementioned Fabric Treatment method may be analyzed via headspace analysis at least three specific touchpoints:

WFO (Wet Fabric Odor, or WET): Wet fabrics are analyzed after the fabric treatment method is finished.

DFO (Dry Fabric Odor, or DRY): Dried Fabrics are analyzed after the fabrics have been line-dried in a closed room for approximately twenty-four hours.

TDFO (Tumble Dry Fabric Odor): Fabrics are analyzed after being dried with a tumble-drying machine (Miele Novotronic T490, selected cycle setting is: "Extra dry setting").

The headspace above the cotton terry tracers is analyzed using SPME headspace GC/MS (gas chromatography mass spectrometry) approach. 4 cm×4 cm aliquots of cotton tracers are transferred to 25 ml headspace vials. The fabric samples are equilibrated for 10 minutes at 65° C. The headspace above the fabrics is sampled via SPME (50/30 μm DVB/Carboxen/PDMS) for 5 minutes. The SPME fiber is subsequently on-line thermally desorbed into the GC. The analytes are analyzed by GC/MS in full scan mode. The total perfume HS response and perfume headspace composition above the tested legs can be determined.

Determination of WFO Index and DFO Index

This method is used to determine the efficiency of a plant-rosin-based perfume delivery system in a treatment composition by comparing headspace analysis data to a comparative composition that includes neat perfume but no plant rosin material.

Two liquid fabric enhancer ("LFE") products, which contain the same type and amount in weight of fragrance material, are used to treat a fabric according to the method provided above. The general formulation of the LFE composition is as follows.

| Ingredient (wt %) | Composition |
| --- | --- |
| Softening active[1] | 7.00%-8.00% |
| Formic acid | 0.045% |
| Sodium hydroxyethane diphosphonic acid | 0.0071% |
| Silicone antifoam | 0.002% |
| Fragrance/PRMs[2] | 0.50%-1.00% |
| Plant Rosin Material[3] | 0.0%-2.3% |
| Water | Balance to 100% |

[1]Diester quaternary ammonium compound (Ci-DEEDMAC = Ditallowoyl Ethoxy Ester Dimethyl Ammonium Chloride [MDEA based, Methyl Di-Ethanol amine based quat, available from Evonik])
[2]Amount of perfume added, irrespective of plant rosin added (if any)
[3]Plant rosin material, if any, is added as a premix with the fragrance material For the product according to Leg A, the fragrance composition is premixed with a plant rosin material (Permalyn 5095, a glycerol ester of a gum rosin, provided in a weight ratio of rosin; fragrance material of from 70:30 to 50:50) and then added a base composition to make the liquid fabric enhancer product. The product according to Leg B does not include a plant rosin material.

| Leg | Description |
|---|---|
| A | LFE formulation containing plant rosin material |
| B | LFE formulation nil plant rosin material |

The two legs of LFE products are used to treat fabrics according to the methods described above. After treatment, fabric odor (Dry Fabric Odor, Wet Fabric Odor, and/or Tumble Dry Fabric Odor, as indicated) is assessed using headspace analysis according to the method provided above.

To determine the perfume delivery efficiency and/or the compatibility of certain perfume raw materials ("PRMs") with rosin plant materials at the WFO touchpoint, the headspace data is used to determine a value for WFO Index defined by the following equation:

$$WFO\ Index = \frac{WFO\ HS_{rosin,i}}{WFO\ HS_{nil\ rosin,i}}$$

where WFO $HS_{rosin,i}$ is the WFO headspace concentration of a given perfume raw material ("i") above fabrics treated with Leg A (e.g., rosin-containing formulation), while WFO $HS_{nil\ rosin,i}$ is the WFO headspace concentration of the same perfume raw material above fabrics treated with Leg B (e.g., nil-rosin formulation). Relatively higher WFO $Index_i$ values indicate that the formulation comprising the plant rosin material is providing freshness benefits for the specific PRM i compared to perfume-only/nil-rosin formulations at the WFO touchpoint.

To determine the perfume delivery efficiency and/or the compatibility of certain perfume raw materials ("PRMs") with rosin plant materials at the DFO touchpoint, the headspace data is used to determine a value for DFO Index defined by the following equation:

$$DFO\ Index = \frac{DFO\ HS_{rosin,i}}{DFO\ HS_{nil\ rosin,i}}$$

where DFO $HS_{rosin,i}$ is the DFO headspace concentration of a given perfume raw material ("i") above fabrics treated with Leg A (e.g., rosin-containing formulation), while DFO $HS_{nil\ rosin,i}$ is the DFO headspace concentration of the same perfume raw material above fabrics treated with Leg B (e.g., nil-rosin formulation). Relatively higher DFO Index values indicate that the formulation comprising the plant rosin material is providing freshness benefits for the specific PRM i compared to perfume-only/nil-rosin formulations at the DFO touchpoint.

Viscosity Method

Viscosity of a liquid composition is measured using a DV-E viscometer from Brookfield. The spindle is automatically spun at a rate of 60 rpm until a stable value is given in centipoise (cP).

Viscosity of the premix comprising rosin plant, delivery agent and potentially emulsifying agent is measured using a HAAKE MARS from Thermo Scientific using a 60 mm 1° C. one and a gap size of 52 micrometers. The shear viscosity at 20 $s^{-1}$ can be obtained from a logarithmic shear rate sweep from 0.01 $s^{-1}$ to 1200 $s^{-1}$ at 21° C. The viscosity may be expressed as centipoise (cP).

Particle Size Determination

Depending on the relative size of the particle, one of two methods is employed: image analysis if the approximate volume-weighted median particle size of the population is 10 μm or greater, or microscopy if the approximate volume-weighted median particle size of the population is less than 10 μm. These methods are described in more detail below.

A. Image Analysis

The volume-weighted median particle size is calculated from images taken from the sample flowing through a variable size flow cell. This instrument is specifically designed for image analysis device for liquid applications (Occhio FC200S). The sample is pumped via a syringe pump at very low speed through the flow cell, while the sample passes through the flow cell images are taken at set times. The speed is matched with the frame speed of the camera and it is dependent on the behaviour of the sample and the particles it contains. The flow cell sizes used were 250 and 500 μm and were depending on the size of the capsules. Detection of the capsules is done via grayscale threshold. Callisto version 2013.13 software is used to read out the pixels and calculate size and shape parameters. The size descriptor used is ISO area diameter.

Illumination is a red-led light source, adjustment of illumination is done manually until proper grayscale detection of the particles is possible. Hardware magnification is dependent on the size of the particles: 6× or 9×.

B. Microscopy

The volume-weighted median particle size of the particles is calculated from the values obtained by microscopically observing and measuring the diameter of around 900 capsules observed in randomly sampled aliquots. The microscope used is the Leica DM6000B. The magnification of the microscope is set to 200×. The outputs obtained after the microscopy analysis are: (1) list of diameters detected; and (2) counts per each diameter size detected.

Therefore, the volume (V) of each particle is calculated with the following equation:

$$V = \frac{4}{3}\pi r^3$$

where r is the radius of each detected particle. Finally, the volume-weighted median particle size is calculated (e.g., via a spreadsheet, such those created in Microsoft Excel™), assuming that each particle is a sphere.

EXAMPLES

The examples provided below are intended to be illustrative in nature and are not intended to be limiting.

Example 1. Exemplary Plant Rosin Materials

Table 1 shows a variety of commercially available plant rosin materials. Additional information is provided where available.

TABLE 1

Exemplary plant rosin materials

| No. | Rosin Type | Derivative Type | Additives | Softening Point (° C.) | Acid Value (mg KOH/g) | TRADE NAME | Mfr.* |
|---|---|---|---|---|---|---|---|
| 1 | Gum Rosin | — | — | 79 | 163 | — | A |
| 2 | Gum Rosin | Glycerol ester | — | 88 | 8 | Permalyn 5095 | B |
| 3 | Gum Rosin | Pentaerythritol ester | — | 125 | 13 | Lurefor 125 | A |
| 4 | Gum Rosin | Pentaerythritol ester | — | 100 | 15 | Permalyn 5110 | B |
| 5 | Gum Rosin | Methyl ester | — | — | 5 | Abalyn D-E | D |
| 6 | Gum Rosin | Hydrogenated | — | 70 | 158 | Staybelite Resin-E | D |
| 7 | Misc. Rosin | Partially Hydrogenated | — | 75 | 168 | Foralyn E | D |
| 8 | Gum Rosin | Partially dimerized | — | 103 | 146 | Poly-Pale | B |
| 9 | Wood Rosin | Hydrogenated glycerol ester | — | 84 | 6 | Foral 85 | C |
| 10 | Wood Rosin | Hydrogenated pentaerythritol ester | — | 99 | 11 | Foral 105 | C |
| 11 | Tall Oil | Saponified sodium soap | — | — | 0.5 | Dresinate TX Rosin Soap | D |
| 12 | Misc. Rosin | Dimerized; Zinc resinate | Zinc salt | 160 | 5 | Zincogral Z | D |

*Mfr. = Manufacturer, according to the following key:

A Luresa Resinas S.L.

B DRT;

C Pinova, Inc.;

D Eastman

Example 2. DFO Performance Comparison of Branched and Unbranched PRMs

This experiment shows how whether a PRM has a branched moiety or not affects freshness performance in treatment compositions according to the present disclosure.

The relative performance of two different PRMs in combination with a plant rosin material in a liquid fabric enhancer ("LFE") treatment composition is tested according to the Fabric Treatment Method, the Headspace Analysis, and Determination of DFO Index test methods provided above.

More specifically, the fragrance composition (perfume oil) comprises undecanal (a linear/unbranched PRM) and methyl nonyl acetaldehyde (a methyl-branched PRM). The tested plant rosin material is Permalyn 5095, a glycerol ester of a gum rosin. After the fabrics (cotton) are treated according to the methods described above, Dry Fabric Odor (DFO) is assessed using headspace analysis according to the method provided above. The results are provided in Table 2 below.

TABLE 2

| PRM (CAS no.) | PRM Structure | DFO Index |
|---|---|---|
| Undecanal (112-44-7) | 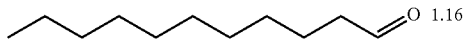 | 1.16 |//

TABLE 2-continued

| PRM (CAS no.) | PRM Structure | DFO Index |
|---|---|---|
| Methyl nonyl acetaldehyde (110-41-8) | 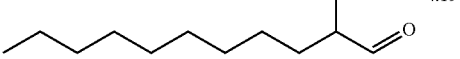 | 4.19 |

As shown in Table 2, the DFO Index results for both PRMs are greater than 1.0, indicating that the formulations that include a plant rosin material perform relatively better at the touchpoint than the formulations that do not include such rosins.

Furthermore, the results in Table 2 show that the presence of a branched methyl moiety leads to improved perfume delivery efficiency of the PRM. Specifically, the DFO index for methyl nonyl acetaldehyde is greater than for undecanal.

Example 3. WFO Performance of Various PRMs

The performance of various PRMs in combination with a plant rosin material in a liquid fabric enhancer ("LFE") treatment composition is tested according to the Fabric Treatment Method, the Headspace Analysis, and Determination of WFO Index$_i$ test methods provided above.

The tested PRMs are listed below in Table 3. The tested plant rosin material is Permalyn 5095™, a glycerol ester of a gum rosin. After the fabrics (cotton) are treated according to the methods described above, Wet Fabric Odor (WFO) is assessed using headspace analysis according to the method provided above. The results are provided in Table 3 below.

TABLE 3

| PRM Name (CAS #) | Chemical Structure | Cycloalkane or Cycloalkene moeity? | Branched alkane moeity? | WFO Index |
|---|---|---|---|---|
| Eucalyptol (470-82-6) | 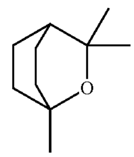 | Yes | Yes | 7.90 |
| Rose oxide L (3033-23-6) | 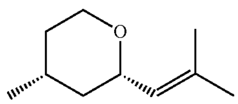 | No | Yes | 5.19 |
| Damascenone total 937459 (23696-85-7) | 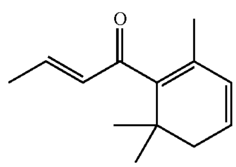 | Yes | Yes | 3.51 |
| Orange oil cold pressed (138-86-3) | 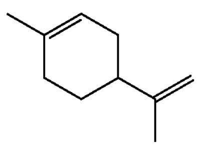 | Yes | Yes | 3.13 |
| Ionone gamma methyl (127-51-5) | 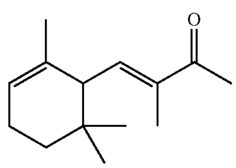 | Yes | Yes | 2.73 |
| Dimethyl benzyl carbinyl acetate (151-05-3) | 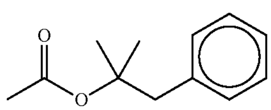 | No | Yes | 2.40 |
| Methyl iso butenyl tetrahydro pyran (16409-43-1) | 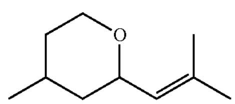 | No | Yes | 2.19 |
| P.t. bucinal (80-54-6) | 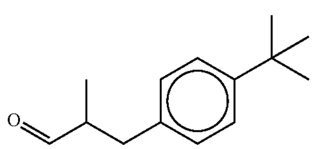 | No | Yes | 2.08 |
| Veloutone (65443-14-3) | 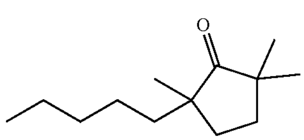 | Yes | Yes | 1.77 |
| Alpha terpineol supra (98-55-5) | 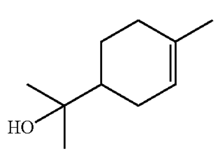 | Yes | Yes | 1.73 |
| Tetra hydro muguol (18479-57-7) | 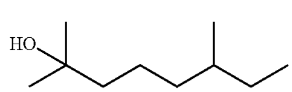 | No | Yes | 1.69 |

TABLE 3-continued

| PRM Name (CAS #) | Chemical Structure | Cycloalkane or Cycloalkene moeity? | Branched alkane moeity? | WFO Index |
|---|---|---|---|---|
| Allyl cyclohexane propionate (2705-76-5) | 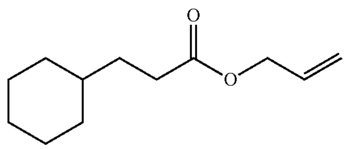 | Yes | No | 1.68 |
| Citronellol (106-22-9) | 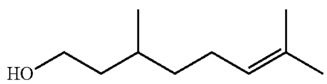 | No | Yes | 1.62 |
| Peonile (10461-98-0) | 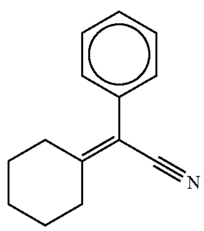 | Yes | No | 1.51 |
| Cashmeran (33704-61-9) | 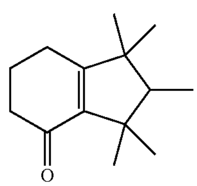 | Yes | Yes | 1.51 |
| Fructalate 943871 (72903-27-6) | 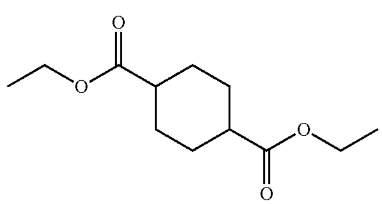 [SMILES: CCOC(=O)C1CCC(C(=O)OCC)CC1] | Yes | No | 1.41 |
| Delta damascone (57378-68-4) | 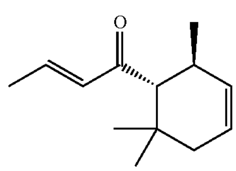 | Yes | Yes | 1.37 |

Example 4. DFO Performance of Various PRMs

The performance of various PRMs in combination with a plant rosin material in a liquid fabric enhancer ("LFE") treatment composition is tested according to the Fabric Treatment Method, the Headspace Analysis, and Determination of DFO Index$_i$ test methods provided above.

The tested PRMs are listed below in Table 4. The tested plant rosin material is Permalyn 5095™, a glycerol ester of a gum rosin. After the fabrics (polyester) are treated according to the methods described above and tumble-dried, DFO Index$_i$) is assessed using headspace analysis according to the method provided above. The results are provided in Table 4 below.

TABLE 4
| PRM Name (CAS #) | PRM Structure | Cycloalkane or Cycloalkene moeity | Branched alkane moeity | DFO Index |
|---|---|---|---|---|
| Dihydro terpinyl acetate (53767-93-4) | 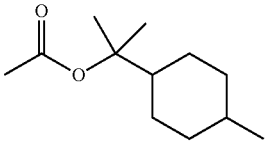 | Yes | Yes | 121.44 |
| Iso Bornyl Acetate (125-12-2) | 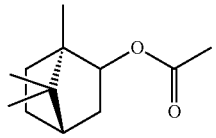 | Yes | Yes | 111.66 |
| Ionone Gamma Methyl (127-51-5) | 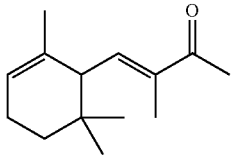 | Yes | Yes | 57.45 |
| Verdox (88-41-5) | 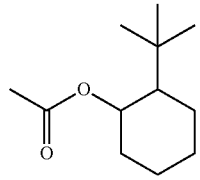 | Yes | Yes | 55.68 |
| Aphermate (25225-08-5) | 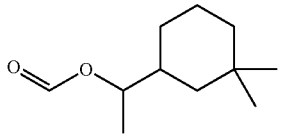 | Yes | Yes | 53.10 |
| Amber Xtreme (476332-65-7) | 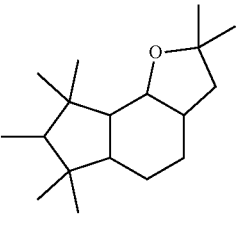 | Yes | Yes | 46.23 |
| Galbascone (56973-85-4) | 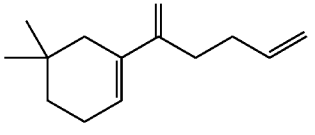 | Yes | Yes | 28.16 |
| Tetra Hydro Linalool (78-69-3) | 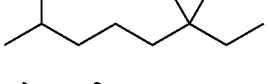 | No | Yes | 24.43 |
| Orange Flower Ether (14576-08-0) | 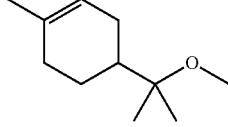 | Yes | Yes | 19.66 |

TABLE 4-continued

| PRM Name (CAS #) | PRM Structure | Cycloalkane or Cycloalkene moeity | Branched alkane moeity | DFO Index |
|---|---|---|---|---|
| Frutene (17511-60-3) | | Yes | No | 11.60 |
| P.T. Bucinal (80-54-6) | | No | Yes | 10.65 |
| iso E super (54464-57-2) | | Yes | Yes | 8.55 |
| Cymal (103-95-7) | | No | Yes | 8.53 |
| Ligustral-2 (27939-60-2) | | Yes | Yes | 7.98 |
| Ligustral-1 (68039-49-6) | | Yes | Yes | 7.88 |
| Methyl dihydro jasmonate (24851-98-7) | | Yes | Yes | 6.33 |
| Cedryl methyl ether (19870-74-7) | | Yes | Yes | 6.13 |
| Adoxal (141-13-9) | | No | Yes | 5.80 |
| Dimethyl benzyl carbinyl butyrate (10094-34-5) | | No | Yes | 5.46 |

TABLE 4-continued

| PRM Name (CAS #) | PRM Structure | Cycloalkane or Cycloalkene moeity | Branched alkane moeity | DFO Index |
|---|---|---|---|---|
| Dupical (30168-23-1) | | Yes | No | 5.40 |
| Flor acetate (5413-60-5) | | Yes | No | 5.27 |
| Undecavertol (81782-77-6) | | No | Yes | 4.97 |
| Methyl nonyl acetaldehyde (110-41-8) | | No | Yes | 4.87 |
| Habanolide (111879-80-2) | | No | No | 3.23 |

It can be noted that the PRMs reported in Table 4 show relatively high DFO $Index_i$ as they provide higher freshness benefits compared to the perfume-only/nil-rosin formulations. It is believed that the reason of the high performance in terms on DFO $Index_i$ is due to the PRM molecular structure. In particular the presence of the cycloalkane or the cycloalkene moiety or the branched alkane moiety leads to improved affinity with the rosin material.

PRMs characterized by cycloalkane or cycloalkene moiety or a branched alkane moiety lead to improved deposition on fabrics, when compared to PRMs who do not contain a cycloalkane moiety, nor do they contain a cycloalkene moiety, as shown below in Example 5.

Example 5. DFO Performance of Comparative PRMs

The following data show relative DFO performance of comparative PRMs. The tests and analysis are run substantially the same as in Example 4. However, none of the PRMs listed below in Table 5 contain a cycloalkane moiety, nor do they contain a cycloalkene moiety, nor do they contain a branched alkane moiety.

TABLE 5

| PRM Name (CAS #) | PRM Structure | DFO index |
|---|---|---|
| Hexyl acetate (142-92-7) | | 1.32 |
| Decyl aldehyde (112-31-2) | | 1.23 |
| Octyl aldehyde (124-13-0) | | 1.15 |
| Undecalactone (104-67-6) | | 0.79 |

It can be noted that the PRMs reported in Table 5 are characterized by a DFO $Index_i$ substantially lower versus the PRMs reported in Table 4. The reason for this lower performance is believed to be due to the PRM molecular structure. In fact, the PRMs of Table 5 do not contain a cycloalkane moiety, nor do they contain a cycloalkene moiety. The absence of this moiety is believed to be responsible for the lower affinity with the rosin material.

Example 6. Correlation of Molecular Descriptors with Performance

The performance of various PRMs in combination with a plant rosin material in a liquid fabric enhancer ("LFE") treatment composition is tested according to the Fabric Treatment Method, the Headspace Analysis, and Determination of DFO $Index_i$ test methods provided above.

The tested PRMs are listed below in Table 6. The tested plant rosin material is Permalyn 5095™, a glycerol ester of a gum rosin. After the fabrics (cotton) are treated according to the methods described above, Dry Fabric Odor (DFO) is assessed using headspace analysis according to the method provided above. The results are provided in Table 6 below.

Additionally, the values of various molecular descriptors are also provided in Table 6, namely SsssCH, dxp10, and Gmin values, as described herein.

TABLE 6

| PRM Name | Molecular descriptor values | | | | |
|---|---|---|---|---|---|
| (CAS #) | SsssCH | dxp10 | Gmin | DFO Index | Rating |
| Dihydro Terpinyl acetate (53767-93-4) | 1.39072 | 0 | −0.271852 | 47.86 | *** |
| Iso Bornyl Acetate (125-12-2) | 0.907963 | −0.0273317 | −0.125394 | 139.00 | *** |
| Verdox (88-41-5) | 0.681852 | 0.0266179 | −0.133195 | 58.88 | *** |
| Mintonat (67859-96-5) | 0.823472 | 0 | −0.143611 | 582.84 | *** |
| Frutene (68912-13-0) | 3.2986 | 0.197041 | −0.0184667 | 25.12 | ** |
| Flor acetate (5413-60-5) | 3.29218 | 0.142192 | −0.10643 | 15.85 | ** |
| Ligustral-2 (27939-60-2) | 0.745324 | 0 | 0.281204 | 7.87 | ** |
| Heliotropin (120-57-0) | 0 | −0.0101735 | 0.247663 | 4.11 | ** |
| Ionone gamma methyl (127-51-5) | 0.426065 | −0.0142079 | 0.18442 | 9.29 | ** |
| Decyl aldehyde (112-31-2) | 0 | 0 | 0.757716 | 1.13 | * |
| Nonyl aldehyde (124-19-6) | 0 | 0 | 0.756076 | 1.05 | * |
| Hexyl cinnamic aldehyde (101-86-0) | 0 | 0.0104167 | 0.901185 | 0.94 | * |
| Octyl aldehyde (124-13-0) | 0 | 0 | 0.753685 | 0.86 | * |
| Undecalactone (104-67-6) | 0.244562 | 0.0680785 | −0.00133513 | 0.79 | * |

The "Rating" values provided in TABLE 6 are assigned as follows:
*** = most preferred, being characterized by SsssCH >= 0.682 and Gmin < −0.106
** = somewhat preferred, being characterized by (a) SsssCH >= 0.682 and Gmin >= −0.106, OR (b) SsssCH <0.682 and dxp10 < −0.00710
* = less preferred, being characterized by SsssCH < 0.682 and dxp10 >= −0.00710

It can be noted that for the "most preferred" materials (Rating=*), the DFO Index values (on cotton DFO) are 1.5 or greater, and for the "somewhat preferred" materials (Rating=), the DFO Index values (on cotton DFO) are between 0.5 and 1.5. Thus, it is believed that the molecular descriptors can be used to suggest or predict PRMs that will perform well.

With regard to the "less preferred" materials (Rating=*), the DFO Index values (on cotton DFO) are less than 0.5. It is worth noting that these "less preferred" PRMs can still provide a freshness benefit to fabrics, but they tend to do so less efficiently in combination with plant rosin materials compared to the most preferred and somewhat preferred PRMs shown here.

Example 7. Additional PRMs, Including Molecular Descriptors

Table 7 includes examples of additional PRMs, including certain molecular descriptors for each. The "Rating" values follow the same criteria as provided in Example 6 above.

TABLE 7

| PRM Name | Cycloalkane or Cycloalkene | Branched alkane | Molecular descriptor values | | | |
|---|---|---|---|---|---|---|
| (CAS #) | moiety | moiety | SsssCH | Gmin | dxp10 | Rating |
| Vertenex (32210-23-4) | Yes | Yes | 0.9726 | −0.135 | 0 | *** |
| Helvetolide (141773-73-1) | Yes | Yes | 0.82389 | −0.4109 | −0.0638 | *** |
| Ethanone, 1-(1,2,3,5,6,7,8,8a-octahydro-2,3,8,8-tetramethyl-2-naphthalenyl)- (68155-66-8) | Yes | Yes | 1.02917 | −0.1361 | 0.11821 | *** |
| Alpha-pinyl isobutyraldehyde (33885-52-8) | Yes | Yes | 1.63988 | −0.1763 | −0.0154 | *** |

TABLE 7-continued

| PRM Name (CAS #) | Cycloalkane or Cycloalkene moiety | Branched alkane moiety | Molecular descriptor values | | | Rating |
|---|---|---|---|---|---|---|
| | | | SsssCH | Gmin | dxp10 | |
| Sandalore (65113-99-7) | Yes | Yes | 1.04535 | −0.1634 | −0.042 | *** |
| Galaxolide (1222-05-5) | Yes | Yes | 1.19347 | 0.25848 | 0.39385 | ** |
| Isocyclocitral (1335-66-6) | Yes | Yes | 1.72463 | 0.23148 | 0 | ** |
| Cyclohexane, 3-ethoxy-1,1,5-trimethyl- (67583-77-1) | Yes | Yes | 1.36023 | 0.49752 | 0 | ** |
| Jasmacyclene (5413-60-5) | Yes | No | 3.29218 | −0.1064 | 0.14219 | ** |
| Verdox (88-41-5) | Yes | Yes | 0.68185 | −0.1332 | 0.02662 | *** |
| Ionone gamma methyl (127-51-5) | Yes | Yes | 0.42607 | 0.18442 | −0.0142 | ** |
| 4-tertiary butyl cyclohexyl acetate (32210-23-4) | Yes | Yes | 0.9726 | −0.135 | 0 | *** |
| Orange oil cold pressed (138-86-3) | Yes | Yes | 0.76732 | 0.76732 | 0 | ** |
| Iso bornyl acetate (125-12-2) | Yes | Yes | 0.90796 | −0.1254 | −0.0273 | *** |
| Cymal (103-95-7) | No | Yes | 0.70134 | 0.12491 | 0 | ** |
| Eucalyptol (470-82-6) | Yes | Yes | 0.82345 | 0.15799 | 0 | ** |
| Allyl cyclohexane propionate (2705-87-5) | Yes | No | 0.76392 | −0.0736 | 0.02515 | ** |
| Methyl cedrylone (32388-55-9) | Yes | Yes | 2.28141 | 0.32604 | 0.15855 | ** |
| Heliotropin (120-57-0) | Yes | Yes | 0 | 0.24766 | −0.0102 | ** |
| Hexamethyl-indanopyran (1222-05-5) | Yes | Yes | 1.19347 | 0.25848 | 0.39385 | ** |
| Nectaryl (95962-14-4) | Yes | Yes | 1.96806 | 0.40463 | 0.08471 | ** |
| Cyclabute (67634-20-2) | Yes | Yes | 3.24266 | −0.0175 | 0.22772 | ** |
| Cetalox (3738-00-9) | Yes | Yes | 1.73319 | 0.20701 | 0.27197 | ** |
| Cedryl methyl ether (19870-74-7) | Yes | Yes | 2.65894 | 0.13771 | 0.13269 | ** |
| Pyranol (63500-71-0) | Yes | Yes | 0.92838 | −0.4883 | 0 | *** |
| Tetra hydro linalool (78-69-3) | No | Yes | 0.76635 | −0.4217 | 0 | *** |
| Ligustral or triplal (68039-49-6) | Yes | Yes | 0.74532 | 0.2812 | 0 | ** |
| Iso gamma super (68155-66-8) | Yes | Yes | 1.02917 | −0.1361 | 0.11821 | *** |
| Orange terpenes (5989-27-5) | Yes | Yes | 0.76732 | 0.76732 | 0 | ** |
| Tetra hydro muguol (18479-57-7) | No | Yes | 0.81699 | −0.4648 | 0 | *** |
| Laevo menthol (2216-51-5) | Yes | Yes | 1.91894 | −0.0289 | 0 | ** |
| Laevo trisandol (28219-61-6) | Yes | Yes | 0.71352 | 0.21831 | −0.0295 | ** |
| Fructalate 943871 (72903-27-6) | Yes | Yes | −0.0451 | −0.1205 | −0.0641 | ** |
| Dimethyl benzyl carbinyl acetate (151-05-3) | No | Yes | 0 | −0.4234 | −0.0165 | ** |
| Delta damascone (57378-68-4) | Yes | Yes | 0.5057 | 0.10194 | −0.0244 | ** |
| Florhydral (125109-85-5) | No | Yes | 0.89313 | 0.33907 | −0.0362 | ** |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A treatment composition comprising a plant rosin material and a fragrance material,
    wherein the fragrance material comprises one or more perfume raw materials,
        wherein the one or more perfume raw materials are selected from the group consisting of: methyl nonyl acetaldehyde; rose oxide L; orange oil cold pressed; ionone gamma methyl; methyl iso butenyl tetrahydro pyran; p.t.bucinal; veloutone; alpha terpineol supra; tetra hydro muguol; allyl cyclohexane propionate; peonile; cashmeran; fructalate 943871; delta damascone; dihydro terpinyl acetate; iso bornyl acetate; ionone gamma methyl; verdox; aphermate; Amber Xtreme; galbascone; orange flower ether; frutene; cymal; ligustral-2; ligustral-1; methyl dihydro jasmonate; cedryl methyl ether; adoxal; dimethyl benzyl carbinyl butyrate; dupical; flor acetate; undecavertol; methyl nonyl acetaldehyde; habanolide; mintonat; heliotropin; vertenex; helvetolide; ethanone, 1-(1,2,3,5,6,7,8,8a-octahydro-2,3,8,8-tetramethyl-2-naphthalenyl)-; alpha-pinyl isobutyraldehyde; sandalore; isocyclocitral; cyclohexane, 3-ethoxy-1,1,5-trimethyl-; jasmacyclene; 4-tertiary butyl cyclohexyl acetate; methyl cedrylone; hexamethylindanopyran; nectaryl; cyclabute; pyranol; iso gamma super; orange terpenes; laevo menthol; laevo trisandol; florhydral; and mixtures thereof;
    wherein the plant rosin material and at least a portion of the fragrance material are co-located in one or more particles,
        wherein the portion of the fragrance material co-located with the plant rosin material in the one or more particles forms a co-located portion of the fragrance material, and
        wherein the co-located portion of the fragrance material comprises at least 50%, by weight of the co-located portion of the fragrance material.

2. The treatment composition according to claim 1, wherein the one or more perfume raw materials are present in an amount of from about 25% to about 100%, by weight of the fragrance materials.

3. The treatment composition according to claim 1, wherein the co-located portion of the fragrance material comprises no more than 50%, by weight of the co-located portion of the fragrance material, of perfume raw materials.

4. The treatment composition according to claim 1, wherein the treatment composition further comprises free fragrance material.

5. The treatment composition according to claim 1, wherein the plant rosin material and the fragrance material are premixed together.

6. The treatment composition according to claim 1, wherein the plant rosin material comprises a material selected from the group consisting of gum rosin, wood rosin, tall oil rosin, derivatives thereof, and mixtures thereof.

7. The treatment composition according to claim 1, wherein the plant rosin material is a plant rosin ester.

8. The treatment composition according to claim 1, wherein the plant rosin material is at least partially hydrogenated.

9. The treatment composition according to claim 1, wherein the treatment composition further comprises a treatment adjunct selected from the group consisting of an amine, a surfactant system, a water-binding agent, a sulfite, fatty acids and/or salts thereof, enzymes, encapsulated benefit agents, soil release polymers, hueing agents, builders, chelating agents, dye transfer inhibiting agents, dispersants, enzyme stabilizers, catalytic materials, bleaching agents, bleach catalysts, bleach activators, polymeric dispersing agents, soil removal/anti-redeposition agents, polymeric dispersing agents, polymeric grease cleaning agents, brighteners, suds suppressors, dyes, hueing agents, free perfume, a perfume delivery system, structure elasticizing agents, fabric softening agents, carriers, fillers, hydrotropes, organic solvents, anti-microbial agents and/or preservatives, neutralizers and/or pH adjusting agents, processing aids, fillers, rheology modifiers or structurants, opacifiers, pearlescent agents, pigments, anti-corrosion and/or anti-tarnishing agents, and mixtures thereof.

10. The treatment composition according to claim 1, wherein the treatment composition is in the form of a liquid composition, a granular composition, a hydrocolloid, a single-compartment pouch, a multi-compartment pouch, a dissolvable sheet, a pastille or bead, a fibrous article, a tablet, a stick, a bar, a flake, a foam/mousse, a non-woven sheet, or a mixture thereof.

11. The treatment composition according to claim 1, wherein the treatment composition is a consumer product composition,
    wherein the consumer product composition is a fabric care composition, a hard surface cleaner composition, a dish care composition, a hair care composition, a body cleansing composition, or a mixture thereof.

12. A method of treating a surface, the method comprising the step of contacting the surface with the treatment composition according to claim 1, optionally in the presence of water.

13. A treatment composition comprising a plant rosin material and a fragrance material,
    wherein the fragrance material comprises one or more perfume raw materials characterized by one of the following parameters:

a. a SsssCH value of ≥0.681852,
  optionally additionally characterized by a Gmin <−0.10643; or
b. a SsssCH value of <0.682 and a dxp10 value of <−0.00709584, wherein the plant rosin material and at least a portion of the fragrance material are co-located in one or more particles, wherein the portion of the fragrance material co-located with the plant rosin material in the one or more particles forms a co-located portion of the fragrance material, and wherein the co-located portion of the fragrance material comprises at least 50%, by weight of the co-located portion of the fragrance material, of one or more perfume raw materials that are selected from the group consisting of: methyl nonyl acetaldehyde; rose oxide L; orange oil cold pressed; ionone gamma methyl; methyl iso butenyl tetrahydro pyran; p.t.bucinal; veloutone; alpha terpineol supra; tetra hydro muguol; allyl cyclohexane propionate; peonile; cashmeran; fructalate 943871; delta damascone; dihydro terpinyl acetate; iso bornyl acetate; ionone gamma methyl; verdox; aphermate; Amber Xtreme; galbascone; orange flower ether; frutene; cymal; ligustral-2; ligustral-1; methyl dihydro jasmonate; cedryl methyl ether; adoxal; dimethyl benzyl carbinyl butyrate; dupical; flor acetate; undecavertol; methyl nonyl acetaldehyde; habanolide; mintonat; heliotropin; vertenex; helvetolide; ethanone, 1-(1,2,3,5,6,7,8,8a-octahydro-2,3,8,8-tetramethyl-2-naphthalenyl)-; alpha-pinyl isobutyraldehyde; sandalore; isocyclocitral; cyclohexane, 3-ethoxy-1,1,5-trimethyl-; jasmacyclene; 4-tertiary butyl cyclohexyl acetate; methyl cedrylone; hexamethylindanopyran; nectaryl; cyclabute; pyranol; iso gamma super; orange terpenes; laevo menthol; laevo trisandol; florhydral; and mixtures thereof.

* * * * *